(12) United States Patent
Lundin et al.

(10) Patent No.: US 10,472,450 B2
(45) Date of Patent: Nov. 12, 2019

(54) ACUTE CARE COVER FOR SEVERE INJURIES

(71) Applicant: The Government of the United States of America, as represented by the Secretary of the Navy, Arlington, VA (US)

(72) Inventors: Jeffrey G. Lundin, Springfield, VA (US); Christopher L. McGann, Glenmont, NY (US); Benjamin C. Streifel, Puyallup, WA (US); Michael G. Stockelman, Silver Spring, MD (US); Chaselynn M. Watters, Silver Spring, MD (US); Christopher J. Santee, Lansdowne, VA (US); Timothy B. Bentley, Rockville, MD (US); James H. Wynne, Alexandria, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 107 days.

(21) Appl. No.: 15/454,267

(22) Filed: Mar. 9, 2017

(65) Prior Publication Data
US 2017/0260314 A1    Sep. 14, 2017

Related U.S. Application Data

(60) Provisional application No. 62/305,671, filed on Mar. 9, 2016.

(51) Int. Cl.
C08F 293/00 (2006.01)
A61L 15/24 (2006.01)
(Continued)

(52) U.S. Cl.
CPC .......... *C08F 293/005* (2013.01); *A61L 15/24* (2013.01); *A61L 15/26* (2013.01);
(Continued)

(58) Field of Classification Search
CPC .................................................. C08F 293/005
See application file for complete search history.

(56) References Cited

U.S. PATENT DOCUMENTS

| | | | |
|---|---|---|---|
| 2002/0042001 A1* | 4/2002 | Lee ........................ | C08G 18/10 429/314 |
| 2011/0008404 A1 | 1/2011 | Lyon et al. | |
| 2012/0202263 A1 | 8/2012 | Blakely et al. | |

FOREIGN PATENT DOCUMENTS

JP    2014108093 A  *  6/2014

OTHER PUBLICATIONS

"Molecular weight characterization of poly(N-isopropylamide) prepared by Living Free-radical polymerization" to Ganachaud et al. Macromolecules 2000, 33, 6738-6745.*

(Continued)

*Primary Examiner* — Michael L Leonard
(74) *Attorney, Agent, or Firm* — US Naval Research Laboratory; Joseph T. Grunkemeyer

(57) ABSTRACT

A compound made by copolymerizing a poly(N-isopropylacrylamide) chain transfer agent, an acrylate salt, and a polyethylene glycol diacrylate. A compound made by copolymerizing a polyethylene glycol, a glycerol ethoxylate, and an aliphatic diisocyanate.

15 Claims, 26 Drawing Sheets

(51) Int. Cl.

| | | |
|---|---|---|
| A61L 15/26 | (2006.01) | |
| A61L 15/42 | (2006.01) | |
| C08G 18/08 | (2006.01) | |
| C08G 18/66 | (2006.01) | |
| C08G 18/73 | (2006.01) | |
| C08J 9/00 | (2006.01) | |
| C08G 101/00 | (2006.01) | |

(52) U.S. Cl.
CPC ............ *A61L 15/425* (2013.01); *C08G 18/14* (2013.01); *C08G 18/6677* (2013.01); *C08G 18/73* (2013.01); *C08J 9/00* (2013.01); *C08G 2101/0083* (2013.01); *C08G 2210/00* (2013.01); *C08J 2205/022* (2013.01); *C08J 2205/044* (2013.01); *C08J 2207/10* (2013.01)

(56) References Cited

OTHER PUBLICATIONS

JP-2014108093_06-2014_English Translation.*

Caihua et al., Synthesis and swelling behavior of thermosensitive hydrogels based on N-substituted acrylamides and sodium acrylate European Polymer Journal 40 (2004) 1075-1080.

Lundin et al. "Multi-Functional Polyurethane Hydrogel Foams with Tunable Mechanical Properties for Wound Dressing Applications" Macromol. Mater. Eng. 2017, 1600375 (Dec. 5, 2016).

Silverstein et al., "PolyHIPEs: Recent advances in emulsion-templated porous polymers" Progress in Polymer Science 39 (2014) 199-234.

Streifel et al., "Porosity Control in High Internal Phase Emulsion Templated Polyelectrolytes via Ionic Crosslinking" J. Poly. Sci. A, 2016, 54, 2486-2492 (Apr. 13, 2016).

Zhang et al., "Synthesis and Characterization of Thermo- and pH-Responsive Double-Hydrophilic Diblock Copolypeptides" Biomacromolecules 2007, 8, 3557-3567.

Search Report and Written Opinion in PCT/US2017/021543 (dated Aug. 29, 2017).

* cited by examiner

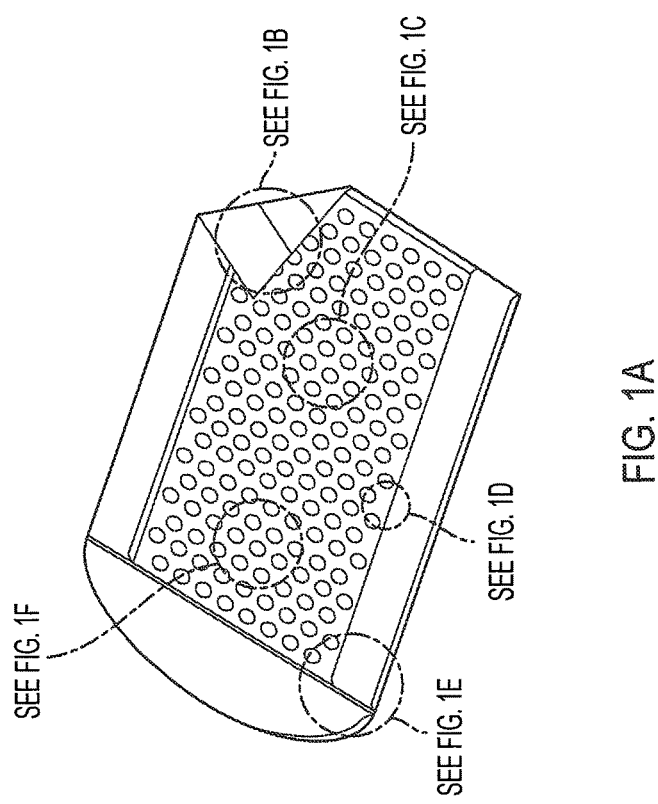

CROSS-LINKED POLYURETHANE HYDROGEL FOAM

ACUTE CARE COVER FOR SEVERE INJURIES

This application claims the benefit of U.S. Provisional Application No. 62/305,671, filed on Mar. 9, 2016. The provisional application and all other publications and patent documents referred to throughout this nonprovisional application are incorporated herein by reference.

TECHNICAL FIELD

The present disclosure is generally related to polymers that may be used in bandages.

DESCRIPTION OF RELATED ART

Severe limb injury and trauma that result from exposure to explosives and shrapnel have increased in both significance and frequency in recent battlefield environments as an unexpected side effect of enhanced body armor and improved military medical response (Belmont et al., *Journal of Trauma-Injury Infection and Critical Care* 2011, 71, E1; Krueger et al., *Journal of Trauma and Acute Care Surgery* 2012, 73, 5438; Dougherty et al., *Injury-International Journal of the Care of the Injured* 2009, 40, 772). Over 30 percent of potentially survivable fatalities in recent combat arenas resulted from hemorrhage due to severe limb trauma (Eastridge et al., *Journal of Trauma-Injury Infection and Critical Care* 2011, 71, S4). Current acute medical interventions fall short in preserving tissue viability and long-term outcomes of warfighters injured in far-forward settings that require extended evacuation times (Holcomb et al., *Annals of Surgery* 2007, 245, 986; Eastridge et al., *Journal of Trauma and Acute Care Surgery* 2012, 73, S431). Current dressing materials were designed for civilian uses which allows for frequent dressing replacement, an option not always available to the injured warfighter. Therefore, a need exists to develop improved materials to serve as wound contact materials in composite multi-functional dressings in order to improve outcomes resulting from severely injured limbs and trauma. Some of the unique challenges that a material must exhibit to achieve multi-functional capabilities in various military applications include antibacterial and antifungal activity, hemostatic properties, and robust mechanical properties that span a large temperature range.

Hydrogels, or hydrophilic polymers that have the capability to absorb water, are an extremely broad class of materials in which numerous compositions and formulations have been developed by many research groups to address a large range of biomedical applications (Hoffman, *Advanced Drug Delivery Reviews* 2002, 54, 3). Often the goal of hydrogel synthesis and design is to impart biodegradability for implanted drug release materials through non-covalent cross-linking or hydrolysable linkages (Hennink et al., *Advanced Drug Delivery Reviews* 2002, 54, 13), however materials that compose wound dressings must remain intact through a variety of temperatures and durations to ensure facile removal and debridement. Polysaccharide-based hydrogels, such as alginate, chitosan, and hyaluronic acid, offer benefits in that they are derived from natural products and afford very large absorption capacities (Utech et al., *J Mater Sci* 2016, 51, 271). Yet, compared to synthetic polymers, potential for chemical modification is limited and as a side-effect of high water absorption capabilities, swollen polysaccharide-based hydrogels also exhibit poor mechanical robustness.

Commercial foam dressings have been found to exhibit uptake capabilities in the range 5.4 to 13.4 g/g, values which fall into the mid-range of other wound dressing type categories (Fulton et al., *Adv. Skin Wound Care* 2012, 25, 315). Foam uptake capabilities have been shown to be dependent on the rate of vapor loss through the exterior of the material, and also foam pore size (Boateng et al., *J. Pharm. Sci.* 2008, 97, 2892). It is important to note the difference between the wound dressing applications to treat chronic wound infection and healing, and those to treat acute traumatic injury in absence of medical care. While many novel materials and effective wound dressings have been developed for the treatment of chronic wounds (Boateng et al., *J. Pharm. Sci.* 2015, 104, 3653), such materials often exhibit properties such as refrigeration requirements, sensitivity to light, or limited shelf-lives, that would likely serve as limitations in potential military arenas.

One class of hydrogels that is promising for wound dressing applications intended for diverse military applications are polyurethane hydrogels. These are based upon the urethane linkages that form the polymers and are capable of exhibit extremely robust material thermal and mechanical stability across a range of challenging environmental conditions. Polyethylene glycol (PEG) is a common component of many polyurethane hydrogel materials for biomedical applications due to its biocompatibility, low toxicity, and resistance to hydrolytic and enzymatic degradation (Ulery et al., *J. Polym. Sci., Part B: Polym. Phys.* 2011, 49, 832; Santerre et al., *Biomaterials* 2005, 26, 7457). Applications other than materials for the treatment of acute wounds include tissue engineering matrices, chronic wound management, stents, catheters, and drug-delivery vehicles.

Several approaches have been taken to achieve antimicrobial activity in hydrogel materials, including but not limited to, silver nanoparticles, antibiotics, antimicrobial agents (Salome Veiga, et al., *Peptide Science* 2013, 100, 637). Other materials exhibit inherent antimicrobial character due to their structure, which while mitigated leaching risks also lacks ability to deliver therapeutics away from the wound dressing (Coneski et al., *Polymer* 2014, 55, 495). Amino acid based monomers have been incorporated into PEG-HDI based polyurethanes to impart biodegradable characteristics to polymerized nanoparticles with tunable temperature sensitivity (Fu et al., *Soft Matter* 2011, 7, 3546).

BRIEF SUMMARY

Disclosed herein is a method comprising: copolymerizing a poly(N-isopropylacrylamide) chain transfer agent, an acrylate salt, and a polyethylene glycol diacrylate, and a compound made thereby.

Also disclosed herein is a method comprising: copolymerizing a polyethylene glycol, a glycerol ethoxylate, and an aliphatic diisocyanate, and a compound made thereby.

BRIEF DESCRIPTION OF THE DRAWINGS

A more complete appreciation will be readily obtained by reference to the following Description of the Example Embodiments and the accompanying drawings.

FIGS. 1A-F illustrate a bandage. FIG. 1A shows the full bandage. FIG. 1B shows an outer layer that may be an $O_2$ permeable, $H_2O$ impermeable, flexible non-woven polymer that provides debris protection. FIG. 1C shows a bio-active portion which may contain hemostatics and antimicrobials having drug efficacy and release kinetics properties. FIG. 1D shows an interface layer between the hydrogel and outer layer that may be electrospun nanofibers containing high MW antimicrobial. FIG. 1E shows a perimeter and tab that may be self-adhesive, conformal while preventing leakage and providing compresion. FIG. 1F shows a hydrogel, which may be absorbent, breathable, antimicrobial, and provide thermal management.

DETAILED DESCRIPTION OF EXAMPLE EMBODIMENTS

Figure 1C:
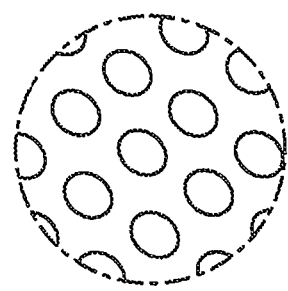
Figure 1F:
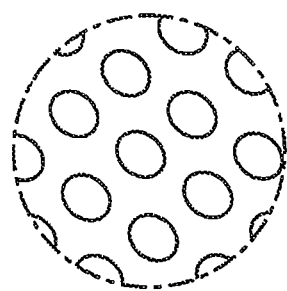
Figure 1D:
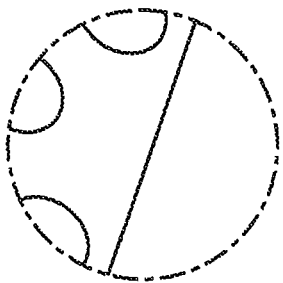
Figure 1B:
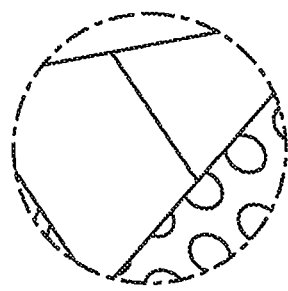
Figure 1E:
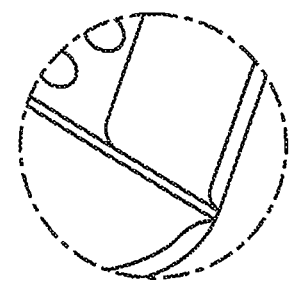

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed are materials suitable for use in a multifunctional bandage affording features that are desirable for use in field applications, where traumatic injury has occurred and medical attention is not easily obtainable within 72 hours. Potential features include, absorbent, compression, breathable, antimicrobial, passive thermal management, flexible, water impermeable, self-adhesive, conformal, leak preventing, compression, hemostatic and ability to release drugs in a very controlled manner. FIGS. 1A-F illustrate an example bandage.

Two approaches may achieve these goals. A block-copolymer hydrogel consisting of a stimuli-responsive poly(N-isopropylacrylamide) (PNIPAM) block covalently linked to a PEG-crosslinked poly(acrylic acid) portion was designed. The polymer composition was tuned to regulate response to thermal and pH stimuli, as well as moderate drug release and exudate absorption kinetics (Belmont et al., *Journal of Trauma-Injury Infection and Critical Care* 2011, 71, E1). Secondly, polyethylene glycol based polyurethane hydrogel foams were also synthesized. Polymerization was tuned to include polyacrylate co-block segments to impart thermo-responsive drug release and improve exudate uptake. A variety of mechanical analyses were performed on both polymer dressings, including DMA, DSC, and compression analysis. Pore size dimensions were measured by SEM. Rates of exudate absorption were simulated with 7.4 pH buffer solutions. Preliminary coagulation studies were performed on whole blood. Drug release kinetics were measured by LC/MS.

Relationships between polymer composition and the rates of exudate absorption, drug release, and hemostasis were identified (Krueger et al., *Journal of Trauma and Acute Care Surgery* 2012, 73, S438). PNIPAM exhibited a lower critical solution temperature (LCST) transition at 32-34° C., resulting in a deswelling of a PNIPAM-containing gel. The LCST can be tuned by altering the properties of the surrounding gel. Internal phase ratios of >77% caused dispersed phase droplets to interconnect and porous polymer scaffolds can be tuned from the micro- to macroporous scale. Absorption of PBS buffer (pH 7.4) was dependent on PEGDA and Ca-acrylate content, but was significantly higher than most other commercial bandage materials. The release rates of swollen gels loaded with cefazolin and doxycycline were dependent on crosslinking density. The rates appeared to be independent of drug identity, in these limited cases. A control gel (no PNIPAM) indicated a single mechanism of release, while a PNIPAM gel indicated two mechanisms (Dougherty et al., *Injury-International Journal of the Care of the Injured* 2009, 40, 772).

A series of polymer formulations have been synthesized that demonstrate a range of physical robustness, hemostatic capabilities, and drug release kinetics. The contribution of each polymeric component in each of the performance factors has been identified to result in an approach from which wound dressing materials of desirable characteristics are synthesized. Likewise, significant progress has been achieved in polymeric material development for both approaches that were taken, the polyurethane hydrogel foam and the stimuli-responsive poly(acrylate) based HIPE gel.

Generally, the poly(acrylate) based HIPE gel is made by copolymerizing a poly(N-isopropylacrylamide) chain transfer agent, an acrylate salt, and a polyethylene glycol diacrylate. Any synthetic method for performing the polymerization may be used, including the methods disclosed herein such as high internal phase emulsion polymerization. The resulting compound may have any physical form, including but not limited to a hydrogel.

The poly(N-isopropylacrylamide) chain transfer agent may be made by a reversible addition-fragmentation chain transfer polymerization of N-isopropylacrylamide with an initiator and a chain transfer agent. Such methods are described herein and otherwise known in the art. One suitable initiator is 2,2'-azobisisobutyronitrile. One suitable chain transfer agent is S-dodecyl-S'-($\alpha,\alpha'$-dimethyl-$\alpha''$-acetic acid) trithiocarbonate. The resulting poly(N-isopropylacrylamide) chain transfer agent may have a number average molecular weight of, for example, 40,000-60,000 g/mol. The final compound may be composed of, for example, 1-20 or 3-15 wt % of residues of the poly(N-isopropylacrylamide) chain transfer agent.

Any acrylate salt may be used, such as alkali metal salts and alkaline earth metal salts. A single salt may be used or combinations of more than one salt may be used. For example, a combination of sodium acrylate and calcium diacrylate may be used. The present of the diacrylate salt leads to additional crosslinking. The final compound may be composed of, for example, 39-60 wt % of residues of the acrylate salts.

The polyethylene glycol diacrylate may have a number average molecular weight of 500-1000. The final compound may be composed of, for example, 28-58 wt % of residues of the polyethylene glycol diacrylate.

Generally, the polyurethane is made by copolymerizing a polyethylene glycol, a glycerol ethoxylate, and an aliphatic diisocyanate. Any synthetic method for performing the polymerization may be used, including the methods disclosed herein. The copolymerization may be performed with or a solvent and under ambient air or nitrogen. It may also be performed as a one pot reaction.

Water may be included as a foaming agent and a surfactant such as a poloxamer may be included. The resulting compound may have any physical form, including but not limited to a hydrogel.

The polyethylene glycol may have, for example, a weight average molecular weight of up to 4000, and the glycerol ethoxylate may have, for example, a number average molecular weight of 500-2000. One example aliphatic diisocyanate is hexamethylene diisocyanate.

The range of the molar ratio of polyethylene glycol to glycerol ethoxylate in the copolymerization may be, but is not limited to, 0.5-6.0. The range of the molar ratio of isocyanate groups to hydroxyl groups used in the copolymerization may be, but is not limited to, 1.0-1.2.

Any of these compounds may be used as part of a bandage or wound care dressing. As used herein, the term "bandage" includes, but in not limited to, gauze pads, strip bandages triangular bandages, adhesive tape bandages, tubular bandages, roller bandages, tension bandages, donut bandages, moleskin bandages, pressure bandages, hydrocolloid dressings, hydrogel dressings, alginate dressings, collagen dressings, long stretch bandages, adhesive bandages, sterile pads, stretch gauze bandages, knuckle bandages, and butterfly closures.

Polyurethane Hydrogel Foam

A polyurethane foam based hydrogel material was made to serve as the internal bioactive layer. A facile reaction scheme (FIG. 2) was developed through a systematic study.

Figure 2:
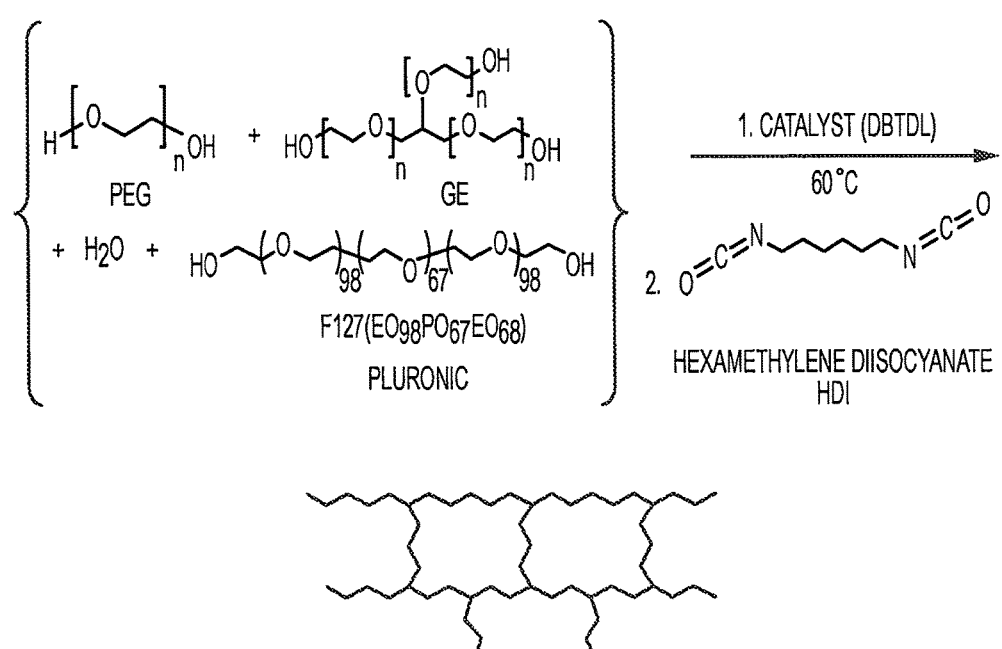
FIG. 2 shows a general reaction scheme for polymerization of cross-linked hydrogel polyurethane foams.

General Preparation of PEG Hydrogel Foams—All solvents were purchased from Fisher Scientific, reagent grade, and used as received. All chemicals were purchased from Sigma-Aldrich (St. Louis, Mo.) and used without further purification. Bacterial strains were obtained from the Naval Medical Research Center. Prior to synthesis, PEG (M=400, 1000, 1500, 3000), glycerol ethoxylate (GE, Mn=1000), and PLURONIC® F-127 poloxamer were dried in a vacuum oven at 45° C. for 2 h. Fixed weights of polyols including PEG, glycerol ethoxylate (GE), and poloxamer were added to a 50 mL conical tube containing a Teflon stir bar and submerged in a 60° C. water bath. The mixture was allowed to vigorously stir for at least 30 min prior to additional of further reagents. Distilled water was then added allowed to mix at for 5 min. Dibutyltin dilaurate (DBTDL) was added to the stirring mixture and after 1 minute, hexamethylene diisocyanate (HDI) was finally added at slight excess (NCO:OH=1.1) while stirring continued until foaming began, typically in less than 1 min. A general reaction scheme is shown in FIG. 2 and detailed compositions of each formulation are presented in Table 1.

TABLE 1

Composition of polyurethane hydrogel foams

| Foam # | Sample ID | PEG (Mw) | PEG:GE (OH Ratio) | PEG:GE (Mole Ratio) | Poloxamer (wt %) |
|---|---|---|---|---|---|
| 6 | PU-400-5:2-0% | 400 | 3:2 | 9:4 | 0 |
| 3 | PU-1000-5:2-0% | 1000 | 3:2 | 5:2 | 0 |
| 4 | PU-1500-5:2-0% | 1500 | 3:2 | 5:2 | 0 |
| 5 | PU-3000-5:2-0% | 3000 | 3:2 | 11:5 | 0 |
| 8 | PU-1000-1:2-0% | 1000 | 1:3 | 1:2 | 0 |
| 9 | PU-1000-3:2-0% | 1000 | 1:1 | 3:2 | 0 |
| 7 | PU-1000-6:1-0% | 1000 | 4:1 | 6:1 | 0 |
| 16 | PU-1000-6:1-1% | 1000 | 4:1 | 6:1 | 1 |
| 14 | PU-1000-6:1-5% | 1000 | 4:1 | 6:1 | 5 |

TABLE 1-continued

Composition of polyurethane hydrogel foams

| Foam # | Sample ID | PEG (Mw) | PEG:GE (OH Ratio) | PEG:GE (Mole Ratio) | Poloxamer (wt %) |
|---|---|---|---|---|---|
| 15 | PU-1000-6:1-10% | 1000 | 4:1 | 6:1 | 10 |
| 19 | PU-1000-6:1-15% | 1000 | 4:1 | 6:1 | 15 |

Characterization—Glass transition temperature ($T_g$) and crystalline phase transitions were determined on a TA Instruments Discovery Differential Scanning calorimeter (DSC). Two successive temperature ramps were then performed from −70° C. to 100° C. at a rate of 10° C./min. Measurements were obtained from the second ramp. A TA Instruments Discovery TGA was utilized to perform thermogravimetric analysis at a heating rate of 10° C./min under $N_2$ from room temperature to 600° C. DSC and TGA data were analyzed utilizing TA Instruments Trios software.

Attenuated total reflectance infrared (ATR-IR) spectra were measured utilizing a Nicolet iS50-FT-IR with iS50 ATR attachment equipped with a Ge crystal from Thermo Scientific (Waltham, Mass.). For each spectrum, 128 scans were compiled.

Pore size measurements of the polyurethane foams were performed on a JEOL JSM-7600F Field Emission SEM (Peabody, Mass., USA) that was operated at an accelerating voltage of 3 kV. PU foams were cut into cross-sections for analysis and were first gold sputter coated with at least 5 nm prior to SEM analysis. Image J was employed to performed pore size measurements on the SEM micrographs.

Compression—PU foams were cut into disks with diameter of 25 mm and thickness of approximately 5 mm. These were placed in a custom built apparatus composed of a section of a conical tube that was solvent welded vertically to a polymer petri dish. This setup served to contain the swelling foam while also allowing for liquid to penetrate to the foam through openings that were punched in the conical tube. Counterpressure was measured with a TA Texture analyzer (UK) equipped with a 1 inch diameter stainless steel cylinder probe. Upon detecting a 0.5 g trigger force, the probe was programmed to compress disk the 3 mm and hold until terminated by the user termination. Immediately upon achieving 3 mm compression, 10 mM PBS buffer solution was poured into the petri dish in which the foam was submerged and force exerted by the swelling foam was monitored.

Buffer Uptake—PU foams were first dried overnight in vacuo prior to uptake experiments. Dry foam samples were then cut, weighed, and placed in 20 mL scintillation vials to which 20 mL of 10 mM PBS buffer solution were added. Each sample was prepared in triplicate. Samples were allowed to reside at room temperature for 24 h, after which the swollen samples were removed from the vials and weighed. Grams uptake per gram of material (g/g) was calculated by dividing the mass gained (final mass—initial mass) by the initial mass of the dry foam.

Drug Release—LC-MS analysis of caffeine release was performed on a Varian 212 LC system connected to a Varian 500 Orbital Trap MS using electrospray ionization (ESI). A PAL autosampler injected samples into a 20 μL sample loop. Separation occurred on an Agilent proshell 120 C8 column with an isocratic mixture of 40% acetonitrile and 60% water, containing 0.1% formic acid, at 200 μL/min. The MS was in positive ionization mode with the following parameters; drying gas temperature of 350° C., shield voltage of 600 V, needle voltage of 5000 V, capillary voltage of 80 V, and m/z range of 190-200. Nitrogen was used for both the drying and nebulizer gas. The system was operated using Varian workstation 6.9.3 software.

Results—The synthesis and optimization of a polyurethane foam based hydrogel material to serve as a robust multifunctional internal bioactive layer of a composite wound dressing material was performed. Polyethylene glycol 1000 (PEG), glycerol ethoxylate (GE), and hexamethylene diisocyanate (HDI) were down selected as the main components of the polyurethane based hydrogel foam. A facile foaming reaction was developed utilizing water as the foaming agent and incorporating PLURONIC® F127 as a surfactant to afford homogenous pore dimensions.

This study examined the properties and behavior of polyurethane foam hydrogels that were synthesized in a one-step and solvent-free procedure. Facile PU chemistry based on linear PEG soft segment, HDI diisocyanate, and GE as a trifunctional PEG cross-linker was selected to leverage simplicity to afford greatest possible viability for scale-up. In addition to these components, a small fraction of water was also introduced into the reaction as the foaming agent through its reaction with isocyanate functional group that evolves $CO_2$. Furthermore, effects of incorporation of the poloxamer at several loading concentrations as a foam stabilizing agent on physical and chemical properties were evaluated. The processing conditions of the reaction were optimized through several trials, eventually identifying the procedure aforementioned in the experimental section in which the rate of polyurethane polymerization and cross-linking occurred on the same scale as the water-isocyanate foaming reaction. The end result was a facile, single step, single pot reaction creating a polyurethane foam.

Figure 3A:
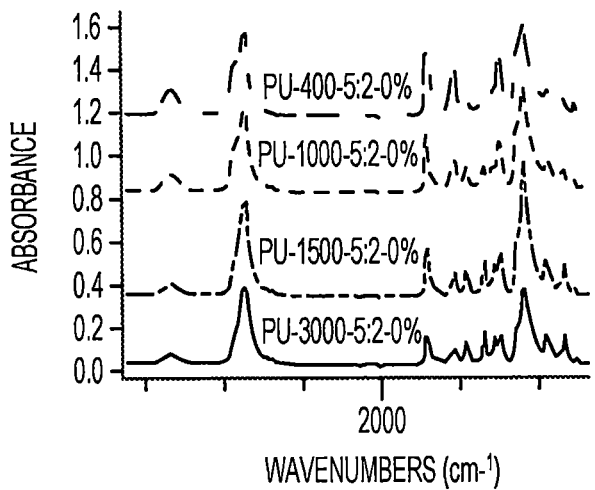
FIGS. 3A-C show IR spectra of foams of increasing PEG length (FIG. 3A), degree of cross-linking (FIG. 3B), and poloxamer loading concentration (FIG. 3C).
Figure 3B:
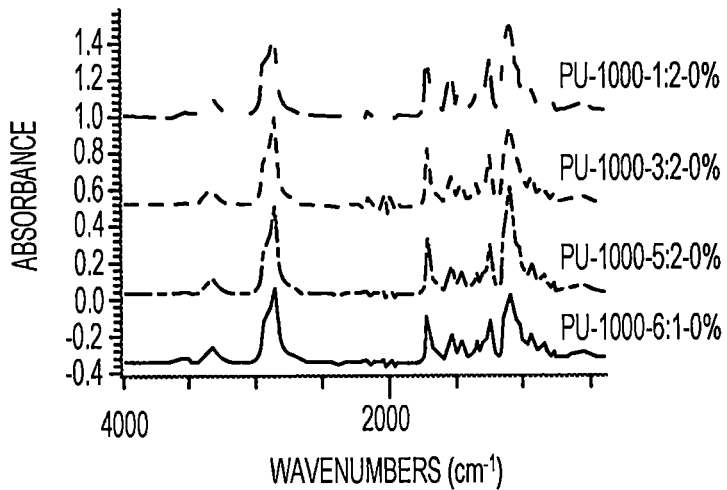
Figure 3C:
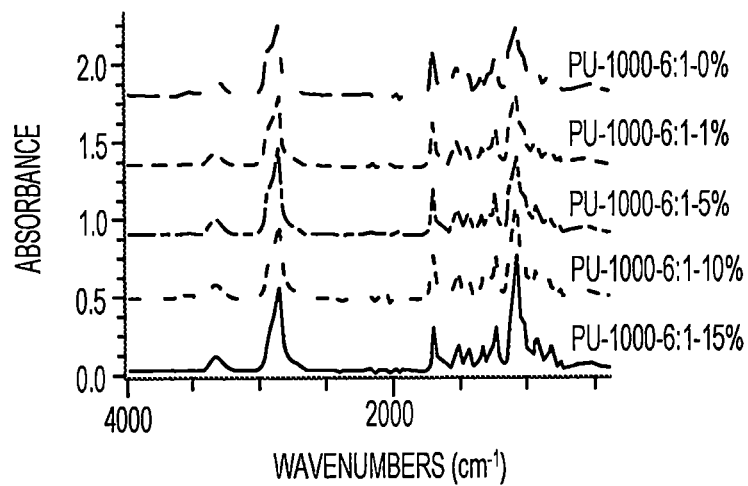

Absence of NCO absorbance at 2200 $cm^{-1}$ in the ATR-IR spectra of polyurethane foams presented in FIGS. 3A-C clearly demonstrate complete reaction and consumption of isocyanate during polymerization of all formulations. This is particularly notable considering that the foaming reaction occurs rapidly, in a single open reaction vessel, and without solvent.

Figure 4:
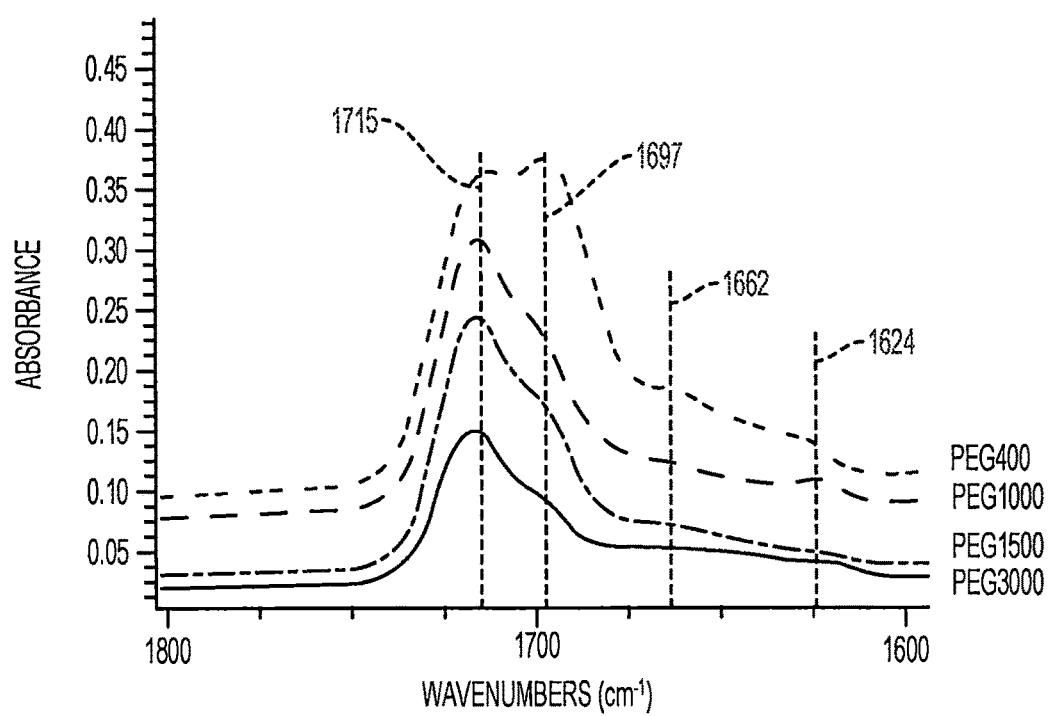
FIG. 4 ATR-IR spectra of carboxylate region of PU foams of increasing PEG length.

FIG. 3A, with increasing PEG Mw of the soft segment, IR absorbance decreased at 1533 $cm^{-1}$ and 1247 $cm^{-1}$, and increased at 1343 $cm^{-1}$ and 1280 $cm^{-1}$. The carbonyl region, 1600-1800 $cm^{-1}$, of the PU foams of increasing PEG length is presented in FIG. 4. Each exhibits relatively strong absorbances at 1715 $cm^{-1}$ that corresponded to amide I C=O stretching attributed to the urethane linkages. The shoulder peak at 1697 $cm^{-1}$ attributed to urea C=O stretching decreased with increasing PEG Mw in the soft segment. Use of water as a foaming agent was expected to result in the formation of urea linkages during polymerization as water reacts with isocyanate, forming $CO_2$ and an amine, which subsequent reacts with an additional isocyanate forming a urea bond. Therefore, decreasing intensity of the urea absorbance of longer PEG lengths indicates fewer amine-isocyanate reactions, likely due to the reduced molecular mobility imparted by the longer chains, especially in a solvent-free reaction. This was supported upon macroscopic observation of the foams, as the longer PEG length PU foams, particularly PEG 3000, exhibited morphologies consisting of large solid areas dispersed with large dispersion of pores. Each also exhibited a minor absorbance at 1624 $cm^{-1}$ resulting from N—H deformation of primary amines, while strongest in PEG 1000 possibly indicating many chain terminations of this particular formulation.

The degree of cross-linking did not have any significant effect on the IR spectra (FIG. 3B) of the polymer formulations, since the IR signature of trifunctional GE cross-linker is similar to that of the PEG soft segment. Increasing concentration of poloxamer resulted in an increasing relative intensity of the ether stretching modes at 1096 cm$^{-1}$ (FIG. 3C) due to the increased contribution of C—O stretching vibrations from the additional ether moieties introduced from the PPO-PEG-PPO structure of poloxamer (James et al., *Biomaterials* 2007, 28, 3182; Roohpour et al., *Materials* 2009, 2, 719; Mishra et al., *Prog. Org. Coat.* 2006, 55, 231; Yen et al., *Macromolecules* 1999, 32, 3068).

Figure 5:
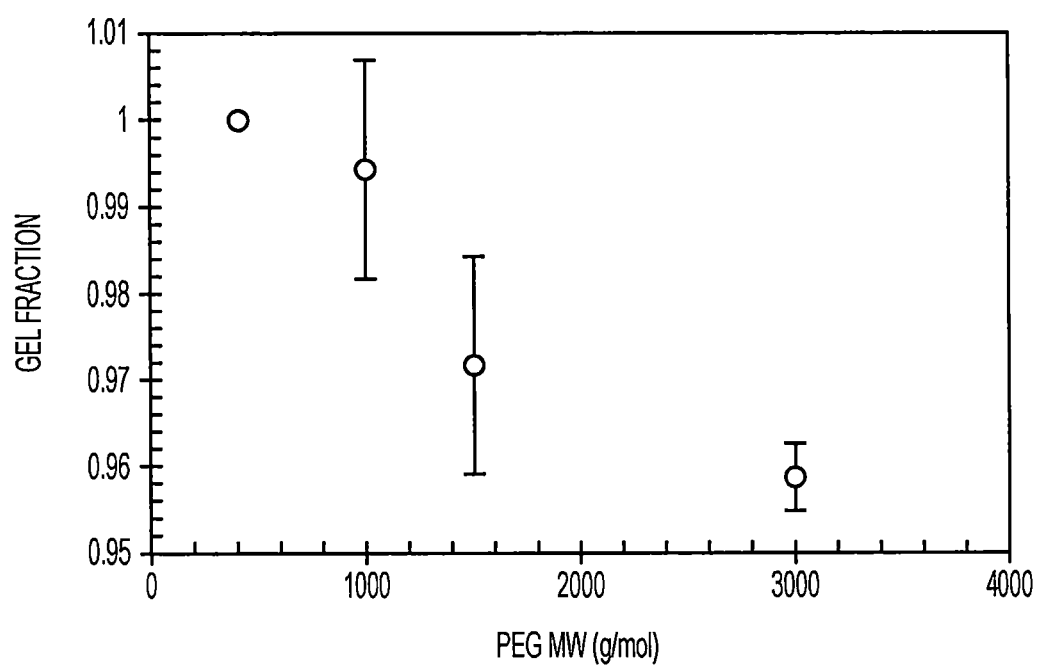
FIG. 5 shows the relationship between gel fraction and the molecular weight of the PEG of PU foams.

A range of thermomechanical analyses were performed on the series of PU foams, the results of which are summarized in Table 2. Supporting the previous ATR-IR spectra, gel fraction analysis indicated that the polymerization reaction of each formulation was relatively complete, as each exhibited a gel fraction greater than 90%. Surprisingly, neither the degree of cross-linking nor the wt. % loading of poloxamer was identified to have an effect on gel fraction. In contrast, an inverse relationship was identified between the molecular weight of the linear PEG monomer and gel fraction (FIG. 5). This was likely due to a decrease in molecular motion due to increasing radius of gyration of growing polymer chain. As the polymerization reaction proceeds, each single mer unit was less likely to be in proximity to an isocyanate group to polymerize. This effect was enhanced as the molecular weight of the PEG monomers was increased.

TABLE 2

Bulk material properties of polyurethane foam hydrogels

| Sample | Gel Fraction (%) | $T_g$ (° C.) | $T_m^1$ (° C.)$^a$ | $T_m^2$ (° C.)$^a$ | Enthalpy $T_m^{1+2}$ (J/g) | Degradation Onset (° C.)$^b$ |
|---|---|---|---|---|---|---|
| 3 | 99.5 | −49.5 | 12.4 | —$^d$ | 40.3 | 313.858 |
| 4 | 97.2 | −46.1 | 28.2 | — | 19.5 | 338.877 |
| 5 | 95.9 | −49.7 | 42.1 | — | 57.4 | 325.307 |
| 6 | 100.0 | −36.2 | — | — | — | 296.347 |
| 7 | 91.9 | −47.8 | 21.5 | — | 39.9 | 322.857 |
| 8 | 100.0 | −45.8 | — | — | — | 317.734 |
| 9 | 94.1 | −47.7 | 16.6 | — | 24.7 | 328.321 |
| 14 | 99.8 | −45.5 | 18.7 | 31.6 | 37.4 | 301.238 |
| 15 | 94.3 | −45.9 | 20.7 | 31.7 | 34.2 | 312.440 |
| 16 | 99.7 | −44.8 | 18.1 | —$^c$ | 31.4 | 304.798 |
| 19 | 98.8 | −46.1 | —$^c$ | 33.8 | 30.2 | 306.887 |

$^a$Peak temperature of endothermic transition based on DSC analysis
$^b$Temperature corresponds to 10% mass loss based on TGA analysis
$^c$Peak obscured as an unresolved shoulder of adjacent peak
$^d$Crystallization exotherm was measured at −26.9° C.

Figure 6A:
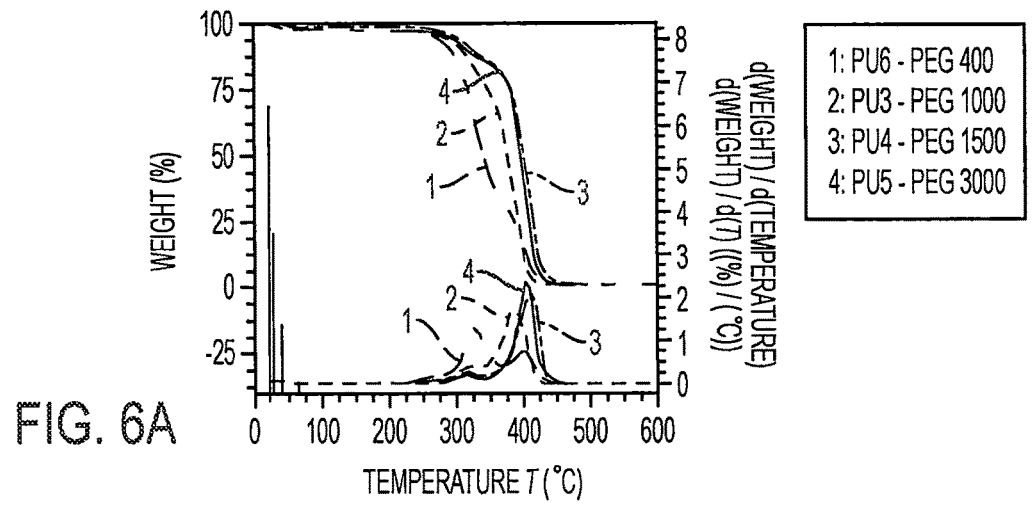
FIGS. 6A-C show TGA analysis of hydrogel foams.
Figure 6B:
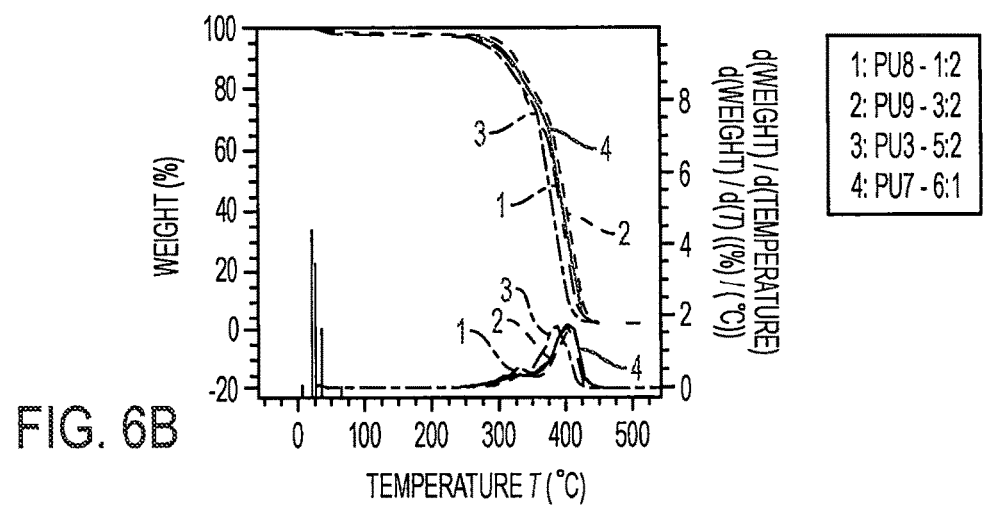
Figure 6C:
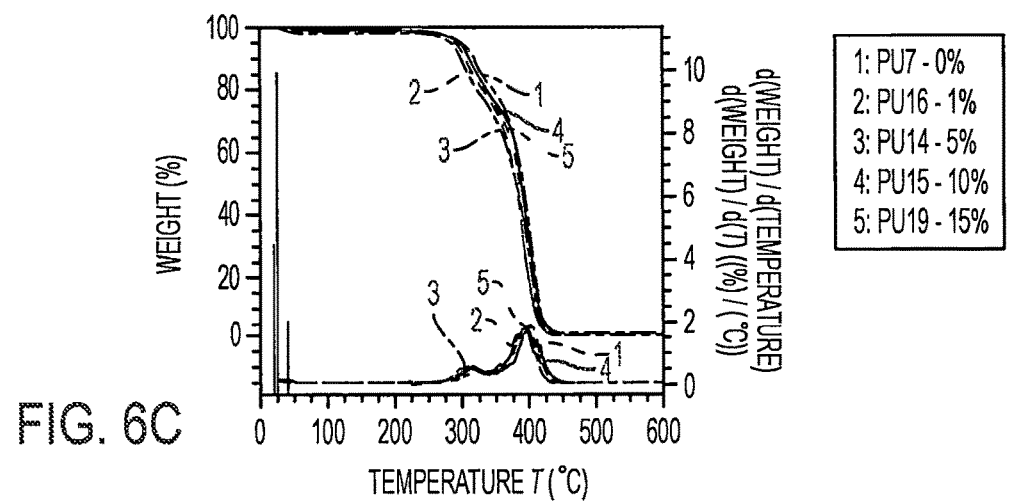
Figure 7A:
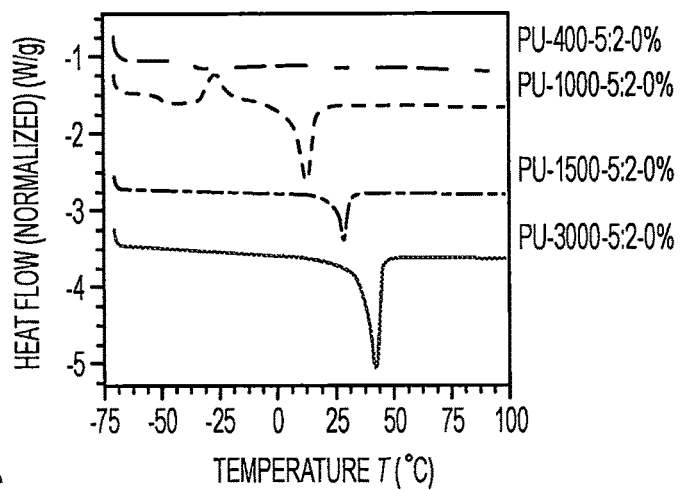
FIGS. 7A-C show DSC analysis of PU foams as a function of PEG length (FIG. 7A), cross-linking ratio (FIG. 7B), and poloxamer concentration (FIG. 7C).
Figure 7B:
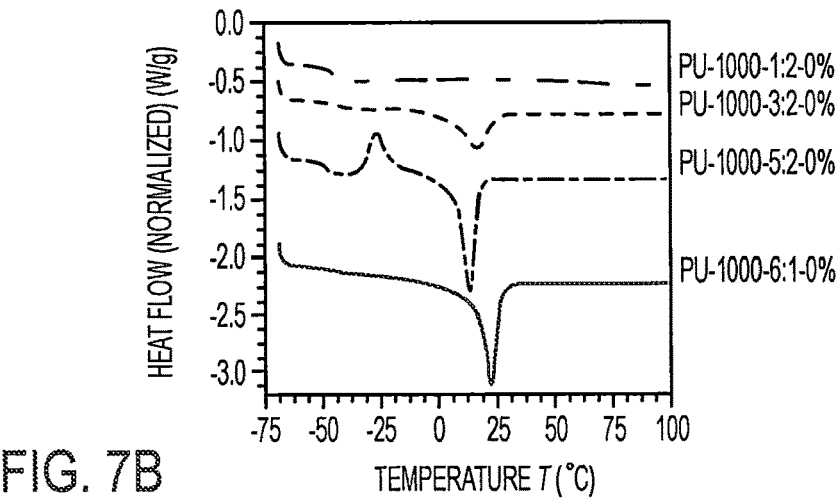
Figure 7C:
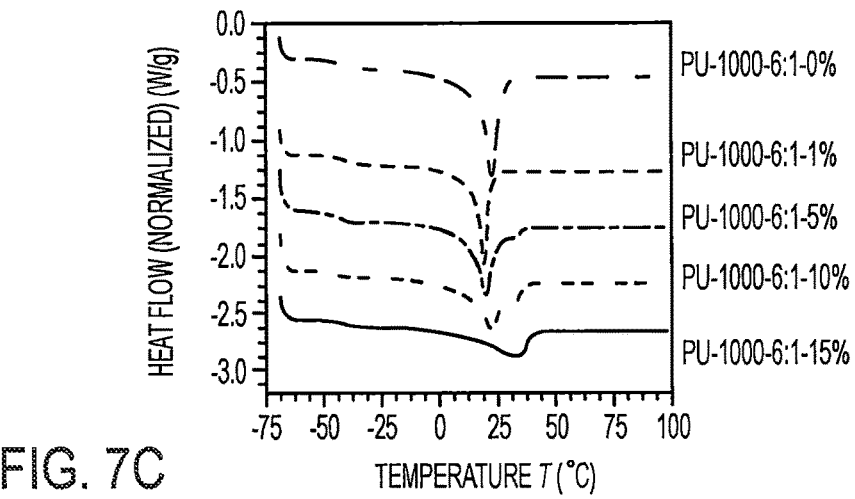

Thermomechanical analyses of the hydrogel foams were performed to assess the environmental stability of the materials. TGA results indicated thermal stability of all the hydrogel foams to greater than 200° C., as shown in FIGS. 6A-C. However, PU foams containing shorter PEG chains exhibited a lower degradation onset temperatures, i.e. 296° C. for PEG 400 compared to 325° C. for PEG 3000. Furthermore, DSC analysis indicated that an endothermic transition occurs at approximately room temperature indicating the disordering of a crystalline phase (FIGS. 7A-C). Qualitative observation of the hydrogel foams ensured that this melting transition was only occurring in the PEG block, as the foams maintained their form to temperatures greater than room temperature.

Figure 8A:
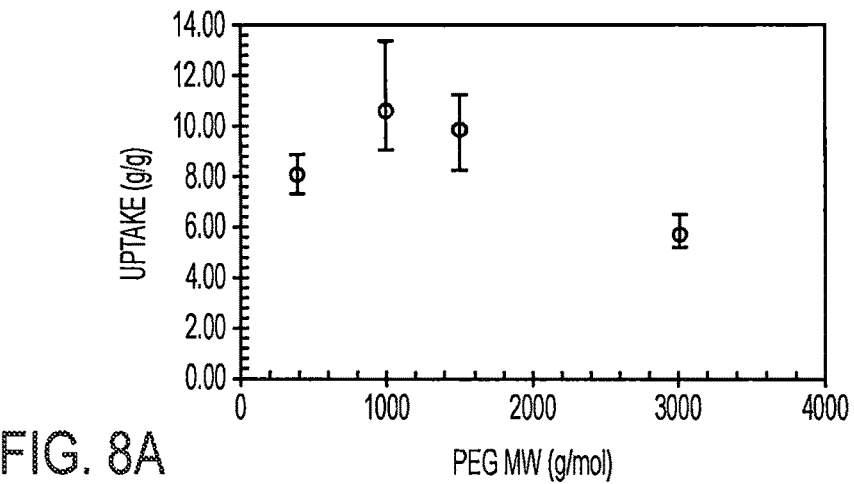
FIGS. 8A-C show the effects that PEG MW (FIG. 8A), degree of cross-linking (FIG. 8B), and concentration of foaming surfactant (FIG. 8C) have on water uptake of polyurethane hydrogel foams.
Figure 8B:
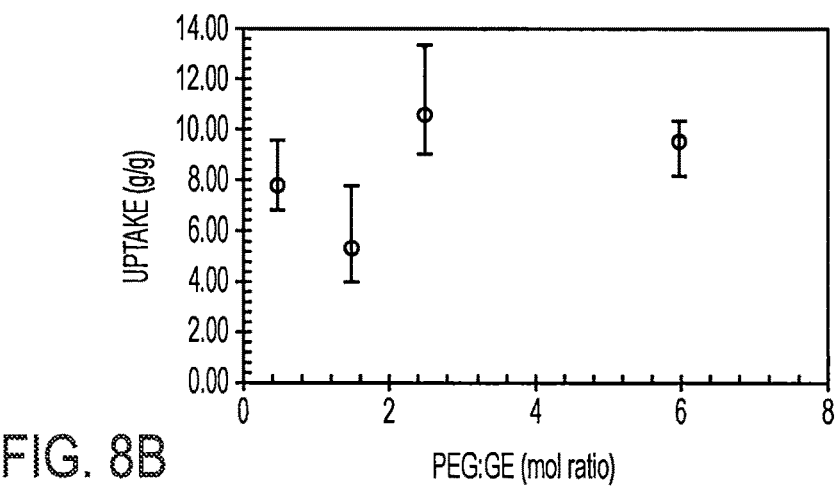
Figure 8C:
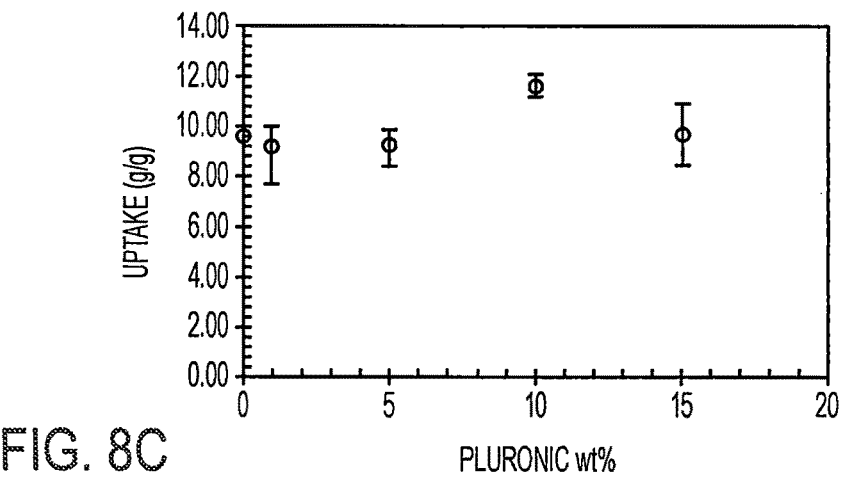

Absorption-Buffer Uptake—The primary criterion utilized to down-select the various components of the foam formulation was water uptake to simulate exudate absorption. FIGS. 8A-C and Table 3 demonstrate the effect that the various components in the hydrogel foam have on uptake. It should be noted that comparable experiments were performed with PBS buffer solution to more accurately simulate exudate absorption and uptakes values remained similar. Of the polyurethane hydrogel foams, water and buffer uptake values of 10-14 g/g were achieved, comparable to commercial polyurethane foam dressings. The advantage of these foams over existing commercial dressings is that the hydrogel foams herein have been designed from the beginning to withstand a variety of environmental conditions.

TABLE 3

Performance evaluation of polyurethane foam hydrogels

| Sample | Uptake (g/g)$^a$ | Max Drug release (ug/mL) | Time to Max release (min) | Avg. pore size (μm ± stdev) |
|---|---|---|---|---|
| 3 | 10.5 ± 2.4 | 14.3 | 60 | 921 ± 257 |
| 4 | 9.9 ± 1.6 | | | 997 ± 318 |
| 5 | 5.6 ± 0.4 | | | — |
| 6 | 8.1 ± 0.8 | 15.5 | 30 | 927 ± 255 |
| 7 | 9.5 ± 1.4 | 15.5 | 10 | 1217 ± 400 |
| 8 | 7.7 ± 0.9 | 21.6 | 30 | 853 ± 304 |
| 9 | 5.3 ± 1.3 | 18.6 | 120 | 906 ± 256 |
| 14 | 9.2 ± 0.8 | 18.25 | 120 | 807 ± 418 |
| 15 | 11.5 ± 0.3 | 13.1 | 180 | 666 ± 248 |
| 16 | 9.2 ± 1.5 | 14.5 | 30 | 884 ± 218 |
| 19 | 9.6 ± 1.2 | 14.3 | 60 | 764 ± 148 |

$^a$PBS buffer uptake over 24 h

Overall, a polyurethane hydrogel foam material has been synthesized with uptake capabilities comparable to commercial foam dressings which are thermally robust and compatible with a variety of chemistries for future modifications such as drug and hemostatic loading.

Stimuli-Responsive Poly(acrylate) Based HIPE-Gel

A stimuli-responsive, super-absorbent poly(acrylate) based gel was made. This approach was followed in order to achieve a super-absorbent material (~100 g/g uptake) that would also exhibit temperature dependent drug release and dosing, a combination of properties that are ideally suited for wound dressing applications.

Figure 9:
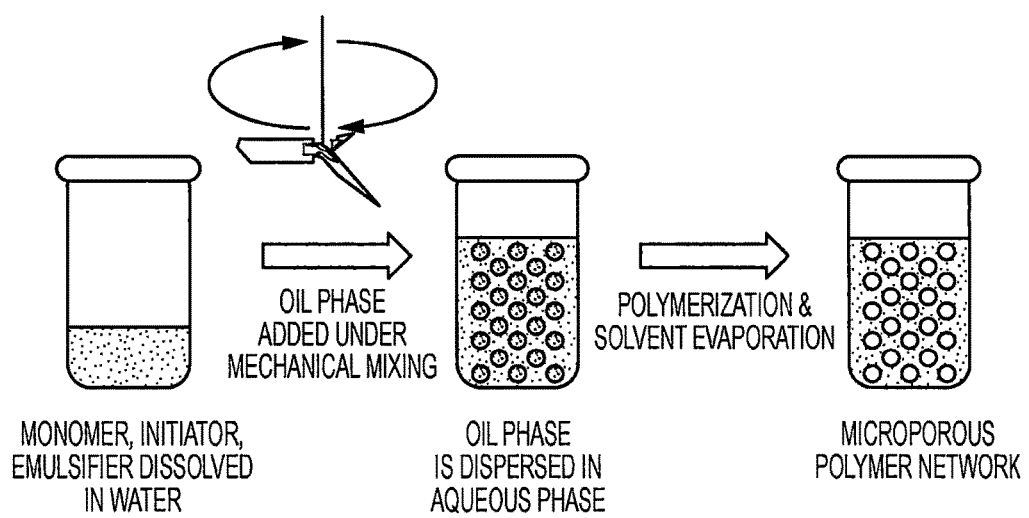
FIG. 9 shows a scheme illustrating HIPE templating method and chemistry of the PNIPAM/polyacrylate/PEGDA foams. Emulsification of the aqueous phase, containing monomer, initiator, and surfactant, with dispersed internal phase, containing toluene, as well as the subsequent polymerization and drying of a cross-linked porous foam is represented.
Figure 10:
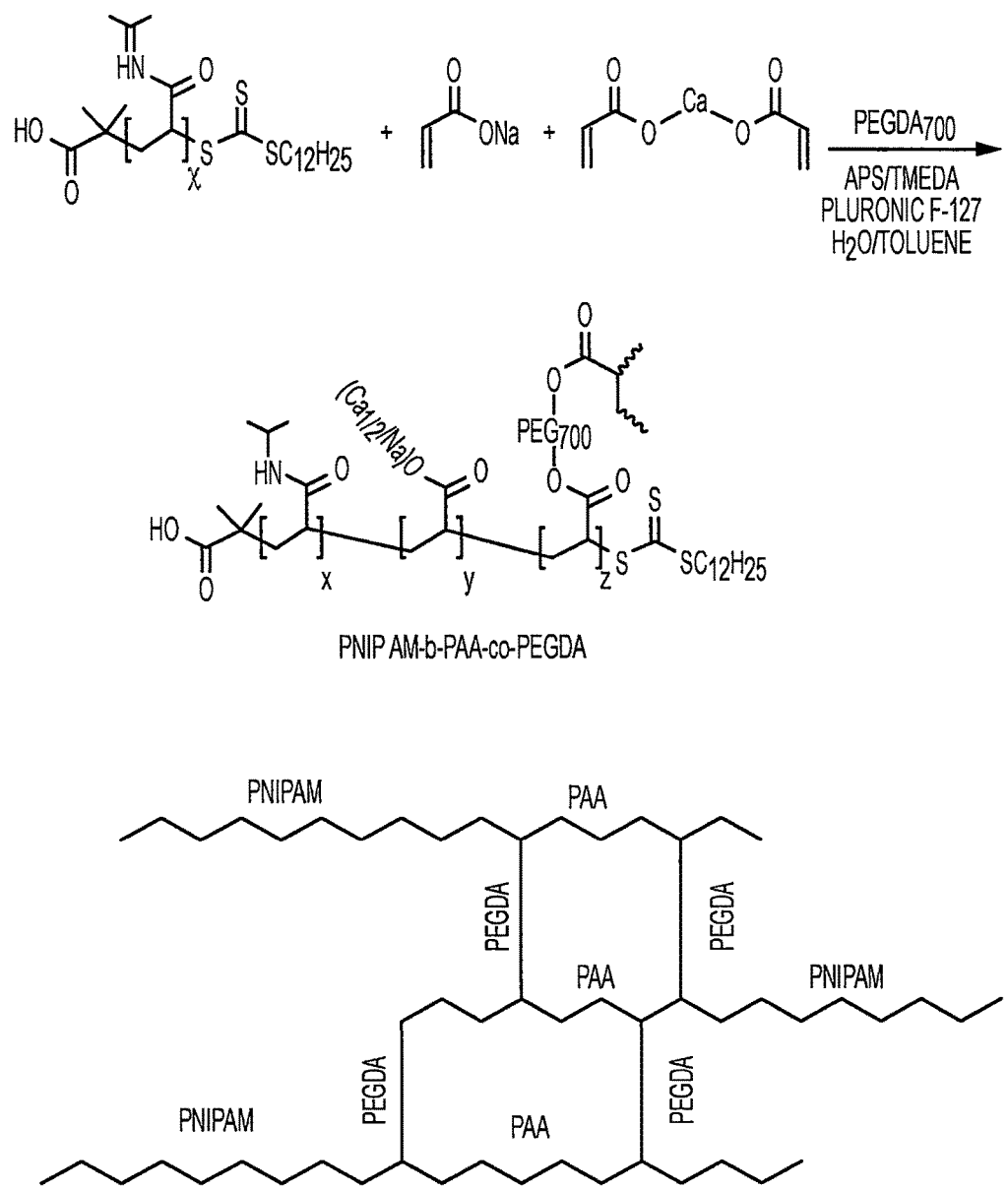
FIG. 10 shows a synthetic scheme for the preparation of multicomponent polyHIPEs.

A facile method of introducing porosity to polymeric materials is accomplished through high internal phase emulsions (HIPEs), a templating method where an internal phase, usually with a high volume fraction (>74% v/v), is dispersed into a continuous phase containing monomer and cross-linker to create a highly viscous, "paste-like" emulsion. Following polymerization of the continuous phase and removal of solvents from both phases, a cross-linked polymer network, or polyHIPE, with interconnected porosity is obtained (FIGS. 9-10) (Silverstein, *Progress in Polymer Science* 39(1) (2014) 199-234; Streifel et al., *Journal of Polymer Science Part A: Polymer Chemistry* 54(16) (2016) 2486-2492; Cameron, *Polymer* 46(5) (2005) 1439-1449). Typically, polyHIPEs have a highly permeable and hierarchical porosity with larger "voids", formed by the dispersed internal phase droplets, connected via smaller "pores". These pores form during the washing and drying steps where polymer film ruptures at thin points between voids (Silverstein; Streifel; Tebboth et al., *Current Opinion in Chemical Engineering* 4 (2014) 114-120). PolyHIPEs have a found numerous applications in the chemical industry as absorbents, insulation materials, reaction supports and separation membranes (Silverstein). More recently, HIPE templating has been utilized in biomedical applications especially in the fields of tissue engineering (Christenson et al., *Biomacromolecules* 8(12) (2007) 3806-3814; Moglia et al., *Biomacromolecules* 12(10) (2011) 3621-3628; Robinson et al., *Tissue Engineering Part A* 20(5-6) (2013) 1103-1112) and drug delivery (Moglia et al., *Macromolecular Rapid Communications* 35(14) (2014) 1301-1305). The remarkable interconnected porosity and facile synthesis that is characteristic of polyHIPEs make the emulsion templating method ideal for the synthesis of highly absorbent materials.

Ammonium persulfate (APS), PLURONIC® F-127 poloxamer, AIBN, sodium hydroxide, calcium oxide, N,N'-tetramethylethylenediamine (TMEDA) and poly(ethylene glycol) diacrylate (PEGDA) were obtained from Sigma Aldrich and used as received, except AIBN, which was recrystallized from methanol. N-isopropyl acrylamide (NIPAM), acrylic acid, tetrahydrofuran (unstabilized), and toluene were obtained from Fisher Scientific and used as received, except for NIPAM, which was recrystallized from hexanes. S-dodecyl-S'-($\alpha,\alpha$'-dimethyl-$\alpha$"-acetic acid) trithiocarbonate (DDMAT) was synthesized according to reported procedures (Lai et al, *Macromolecules,* 2002, 35, 6574-6756). PNIPAM (49,800 g/mol Mn) was synthesized by RAFT polymerization with DDMAT, AIBN, and NIPAM in toluene, and precipitated twice from boiling diethyl ether (Zhang et al., *Biomacromolecules,* 2007, 8, 3557-3567). Sodium acrylate and calcium diacrylate were synthesized as published (Raju et al., *Polym. Int.,* 2001, 50, 946-951). Deionized water was used unless stated otherwise.

A representative polymerization reaction is detailed as follows. (Specifics for each polyHIPE variation can be found in Table 4.) Sodium acrylate (1.00 g, 10.6 mmol), calcium diacrylate (0.194 g, 1.06 mmol), PEGDA (1.33 mL, 2.13 mmol), ammonium persulfate (APS, 48 mg, 0.213 mmol), and PLURONIC® F-127 (55 mg) were placed into a vial and stirred in DI water (10 mL) until dissolved. PNIPAM-CTA (100 mg, 57,300 Mw, 49,800 gmol$^{-1}$ Mn, 1.15 Đ) was stirred in THF (1.0 mL) until dissolved. Both solutions were placed in a 100-mL 3-neck flask with overhead mechanical stirrer (IKA Model RW20) equipped with a PTFE paddle. The mixture was sparged with $N_2$ for 30 min before stirring at 1000 RPM. $N_2$-sparged toluene (40 mL) was added slowly, and the thick, white emulsion stirred at ambient temperature for 30 min before addition of TMEDA (0.03 mL, 0.213 mmol). The viscous emulsion was stirred for 10 s before pouring into PTFE-coated aluminum weigh pans (VWR) and capped with another PTFE-coated aluminum pan. The HIPE mixture was allowed to polymerize at room temperature for 48 h before being removed from the pans, cut into cylinders or strips, and air dried for 48-72 h. Remaining solvent was removed in vacuo at ambient temperature for 24 h.

Figure 11:
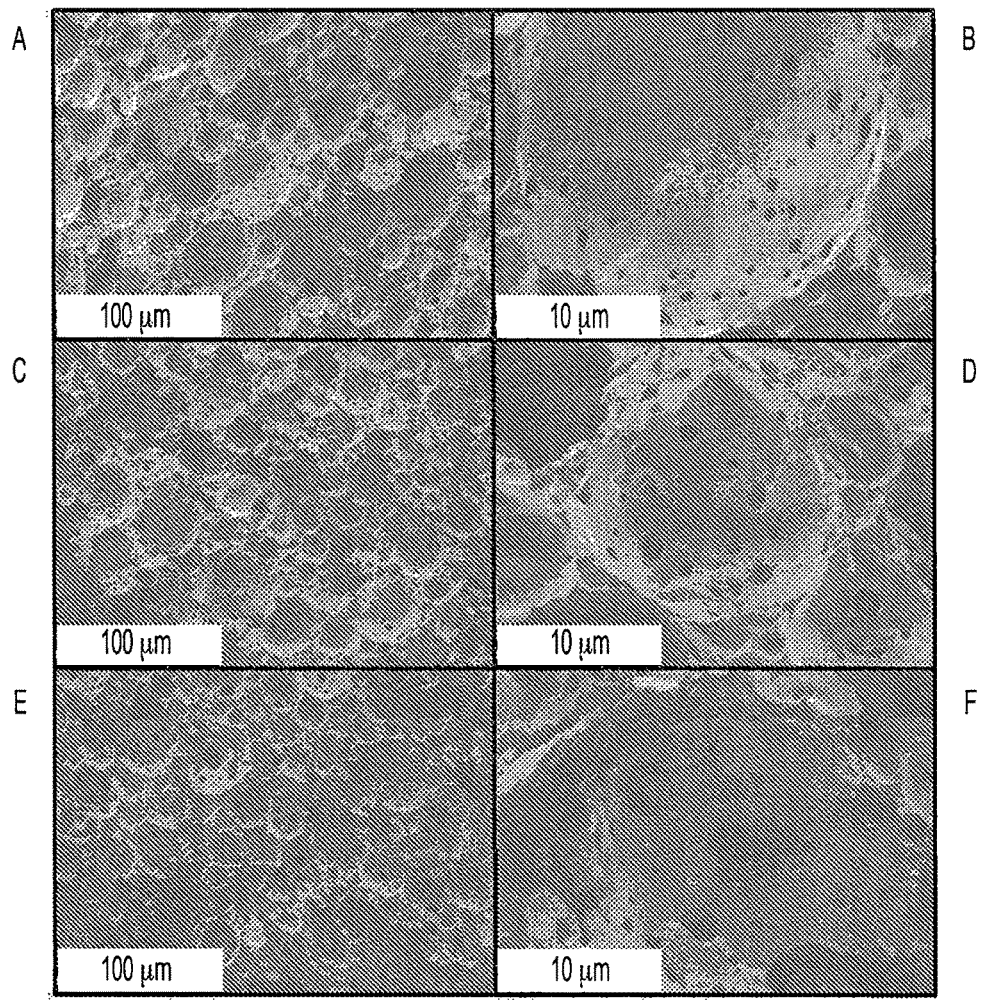
FIG. 11 shows scanning electron micrographs showing typical polyHIPE morphology and variation of void and pore size depending on $Ca^{2+}$ diacrylate content (10 wt % PNIPAM, 20 mol % PEGDA). A and B: 0.1 equiv., C and D: 0.2 equiv., E and F: 0.3 equiv.

Reversible addition-fragmentation chain-transfer (RAFT) polymerization was utilized to achieve control over the molecular weight of PNIPAM. A lower critical solution temperature (LCST) transition at 32-34° C. results in deswelling of a PNIPAM-containing gel. The LCST can be tuned by altering the properties of the surrounding gel. RAFT polymerization of NIPAM yielded a macro-CTA that was easily polymerized in a high internal phase emulsion (HIPE) gel template. Drying yielded porous, high surface area gels (FIG. 11).

Figure 12A:
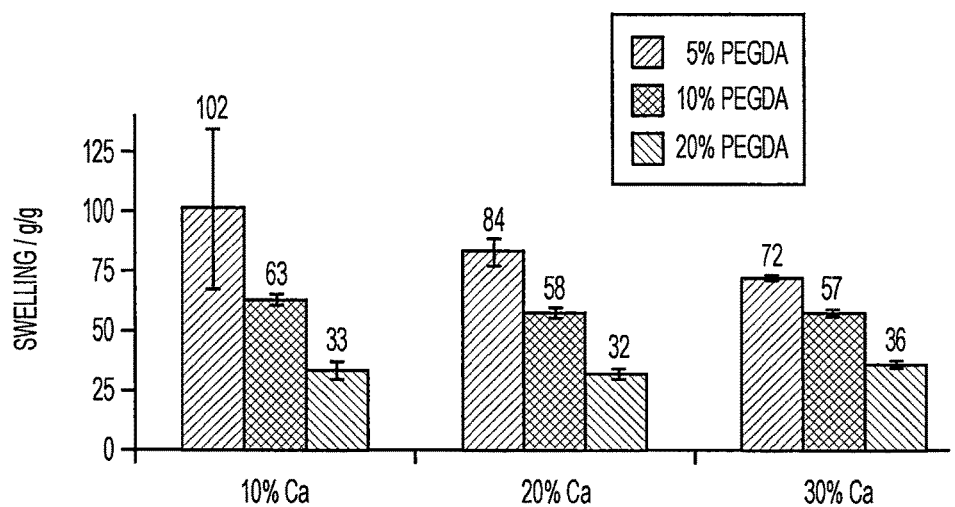
FIG. 12A shows PBS buffer (pH 7.4) uptake by HIPE-gels containing increasing cross-linker (PEGDA) and Ca concentration.

This synthetic procedure was selected to afford a microporous scaffold that would allow for very high exudate uptake capabilities. Exudate uptake was simulated with a PBS buffer solution at pH 7.4. In these studies, it was found that absorption of PBS buffer (pH 7.4) was dependent on PEGDA and Ca-acrylate content (FIG. 12A). The uptake values that were observed were also significantly higher than most other commercial bandage materials. The porosity is highly tunable based upon conditions of the RAFT and HIPE reaction.

Figure 12B:
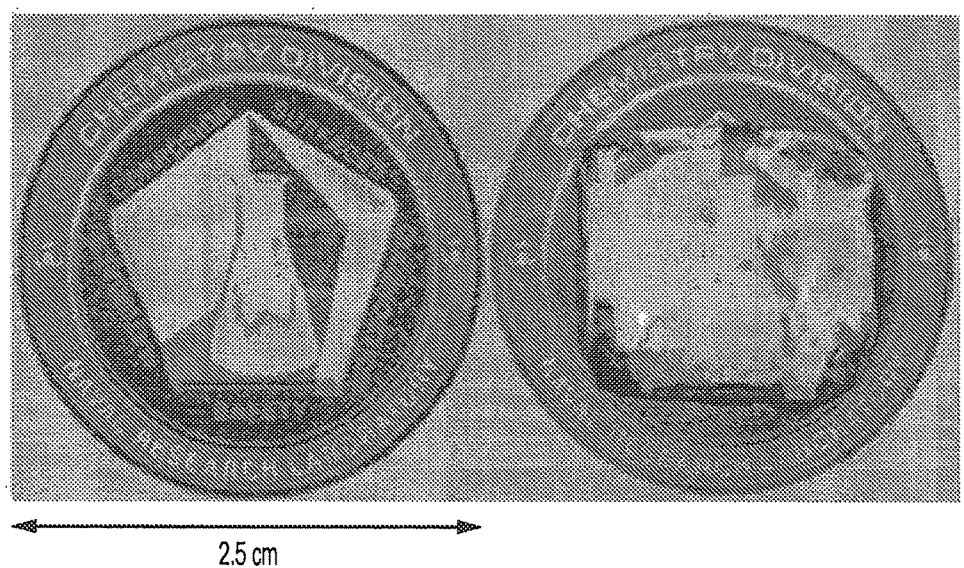
FIG. 12B shows that upon swelling with water, the gels increase in volume and become optically transparent

Upon absorption of water, the synthesized gels become optically transparent (FIG. 12B). Optical transparent would allow for inspection of a wound site without the removal of the protective wound dressing. Furthermore, the volume of the gel significantly increases upon swelling. This affords the potential for the material to impart compression when utilized in a wound dressing material.

Figure 13A:
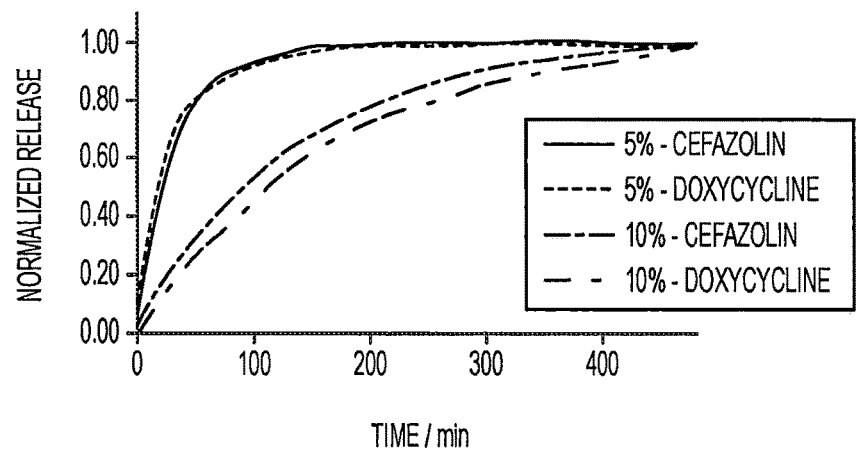
FIG. 13A shows drug-release kinetics dependence on cross-linking density.
Figure 13B:
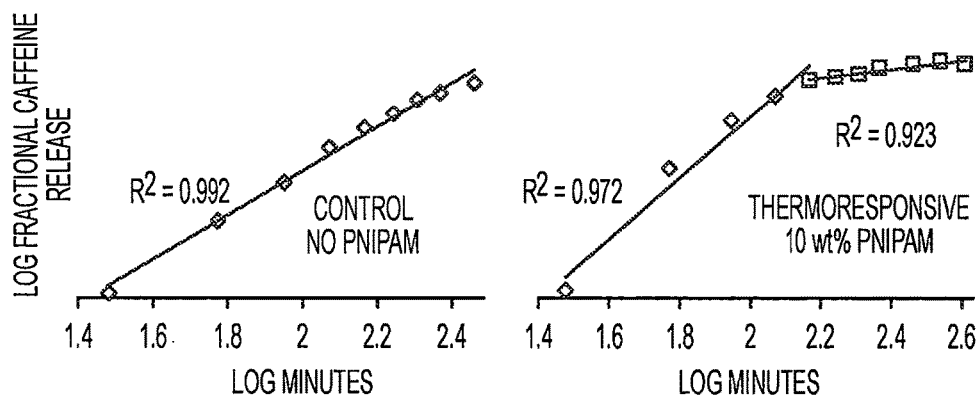
FIG. 13B shows demonstration of the thermoresponsive drug release kinetics due to NIPAM incorporation.

The drug release kinetics of the gels have also been investigated. First, the synthesized gels were soaked in solutions of drugs and subsequently dried to load the gels. Drug release was monitored by LC/MS. Preliminary studies were performed utilizing caffeine as a simulant compound for antimicrobials. The release rates of swollen gels loaded with cefazolin and doxycycline were dependent on cross-linking density. The rates appeared to be independent of drug identity, in these limited cases (FIG. 13A). The release kinetics of the gels were also investigated as a function of temperature. A control gel (no PNIPAM) indicated a single mechanism of release, while a PNIPAM gel indicated two mechanisms (FIG. 13B).

Figure 14:
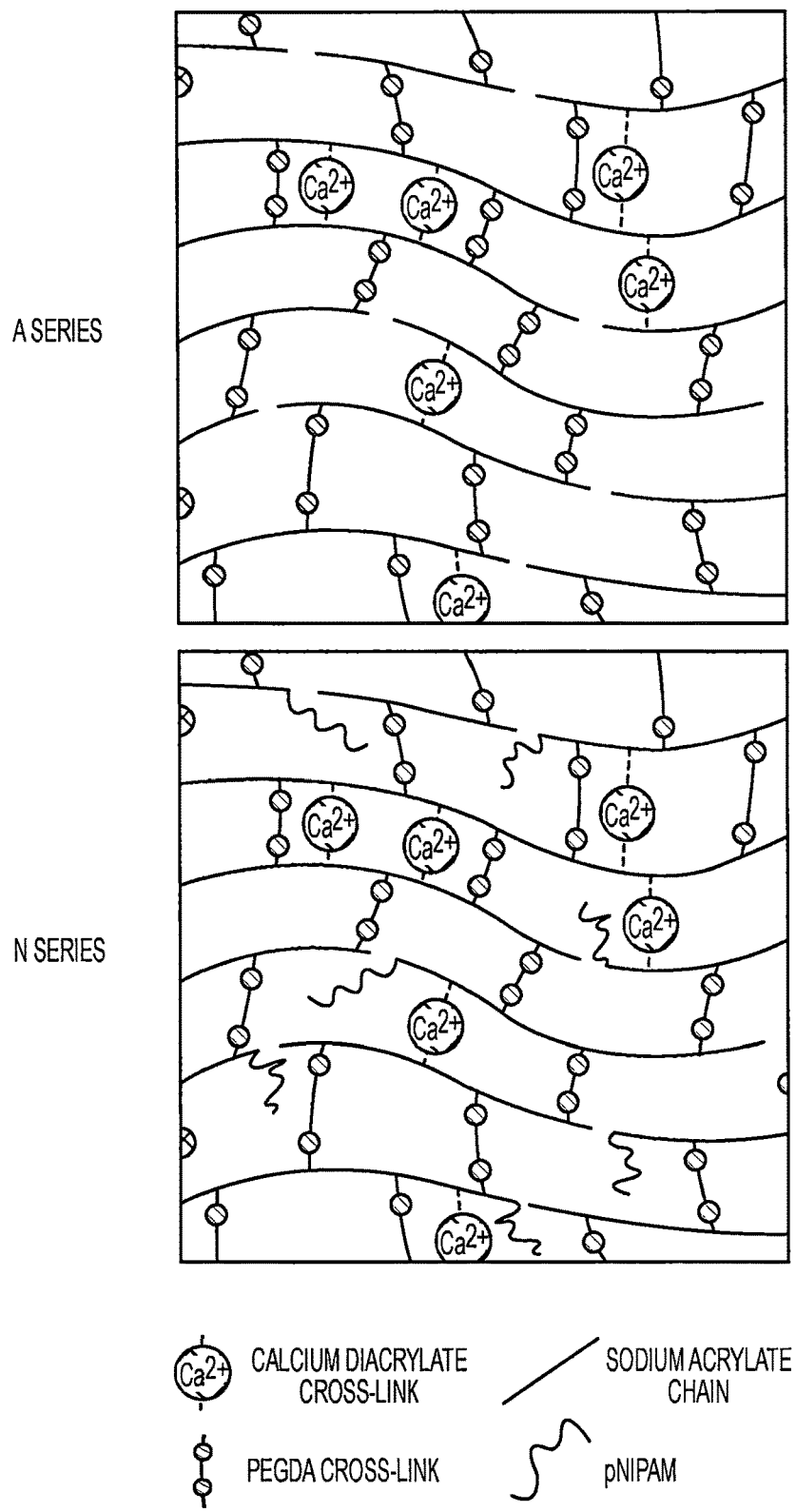
FIG. 14 illustrates a cross-linked network.

As illustrated by FIG. 14 and Table 5, two classes of polyHIPEs were investigated: the A series, which were composed of sodium acrylate and calcium diacrylate (at a 10:3 molar ratio) with increasing concentrations of PEG diacrylate, and the N series, which mirrored the A series but includes 30 wt % NIPAM prepolymer. To simplify the discussion, an alphanumeric naming convention was

TABLE 4

Reagents used in the synthesis of the polyHIPE materials

| Entry | Na acrylate (g) | PNIPAM (g) | Ca acrylate (g) | PEGDA (g) | APS (g) | TMEDA (mL) | Poloxamer (g) | H$_2$O (mL) | Toluene (mL) |
|---|---|---|---|---|---|---|---|---|---|
| 1 | 1 g | 0 | 0 | 1.49 g | 0.024 | 0.03 | 0.055 | 10 | 40 |
| 2 | | | 0.194 | (0.2 eq) | | | | | |
| 3 | | | 0.387 | | | | | | |
| 4 | | | 0.581 | | | | | | |
| 5 | | 0.1 | 0 | | | | | | |
| 6 | | | 0.194 | | | | | | |
| 7 | | | 0.387 | | | | | | |
| 8 | | | 0.581 | | | | | | |
| 9 | | 0.3 | 0 | 0.745 g | | | | | |
| 10 | | | 0.194 | (0.1 eq) | | | | | |
| 11 | | | 0.387 | | | | | | |
| 12 | | | 0.581 | | | | | | | devised: the A or N refers to the acrylate-only or NIPAM-containing polyHIPEs, respectively, and the number refers to the PEG diacrylate content in tenth molar equivalents of sodium acrylate (e.g. N3 would be NIPAM-containing poly-HIPE cross-linked with 0.3 moles of PEDGA for every mole of sodium acrylate).

TABLE 5

PolyHIPE Composition

| | PNIPAM | HIPE Code | Na Acrylate | Ca Diacrylate (mole equivalence) | PEG700 Diacrylate |
|---|---|---|---|---|---|
| A Series | 0 wt% | A2 | 1 | 0.3 | 0.2 |
| | | A3 | 1 | 0.3 | 0.3 |
| | | A5 | 1 | 0.3 | 0.5 |
| N Series | 30 wt% | N2 | 1 | 0.3 | 0.2 |
| | | N3 | 1 | 0.3 | 0.3 |
| | | N5 | 1 | 0.3 | 0.5 |

The NIPAM prepolymer was synthesized via RAFT using standard protocols (Lai et al., *Macromolecules* 35(18) (2002) 6754-6756) and added to the other monomeric precursors during synthesis; as such, the PNIPAM block, with a number average molecular weight of approximately 50 kDa, formed dangling chain ends in cross-linked polyHIPE network (FIG. 14). Initially, the PNIPAM block was included to impart the polyHIPEs with thermoresponsive behavior as a means of controlling drug delivery; unfortunately, the thermoresponsive behavior was muted when cross-linked into polyHIPEs (data not shown). However, PNIPAM has displayed self-emulsifying behavior in other HIPE systems and was included to improved emulsion stability. The backbone of the polyHIPE networks was designed to comprise polyacrylate salts due to their high capacity for water absorption. The ability to absorb excess fluid was a critical design consideration since the target application of these dressings would be severe injuries complicated by significant quantities of wound exudate. In fact, polyacrylates are a classic example of superabsorbent polymers (Chen et al., *Journal of Applied Polymer Science* 75(11) (2000) 1331-1338; Sohn et al., *Journal of Applied Polymer Science* 87(2) (2003) 252-257) and ideally suited for this application. The incorporation of calcium diacrylate was motivated by calcium's role as mediator of hemostasis (Varga-Szabo et al., *Journal of Thrombosis and Haemostasis* 7(7) (2009) 1057-1066); increased local calcium concentration stimulates rapid coagulation through platelet aggregation as well as by acting on clotting factors VII, IX and X (Hattori et al., *Annals of Biomedical Engineering* 38(12) (2010) 3724-3732). PEG diacrylate was included as a hydrophilic, relatively inert cross-linker, responsible for the covalent network which maintains the integrity of the material when swollen with fluid.

Prepared samples were mounted on sample stubs with adhesive copper tape, and subsequently sputter coated with 10 nm Au (Cressington 108 Auto, Ted Pella, Redding, Calif.). Scanning electron microscopy (SEM) was performed using a JEOL-7600F field emission SEM, and images were collected with PC SEM software. ImageJ (National Institutes of Health, Bethesda, Md.) was used to measure void and pore diameters. Twenty five voids (spherical voids where toluene phase was located before drying) and twenty five pores (interconnecting pores between toluene droplets) were measured and the values averaged for each polyHIPE. A statistical correction was applied to the pore size measurements, due to hemispherical nature of the voids (Cameron et al., *Colloid. Polym. Sci.*, 1996, 274, 592).

The chemical state and relative concentrations of C, O, N, Ca, Na, and S were assessed by X-Ray photoelectron spectroscopy (XPS) using a Thermo Scientific K-Alpha X-ray photoelectron spectrometer at a chamber pressure $<5.0 \times 10^{-8}$ ton and equipped with a monochromatic Al K$\alpha$ source (1486.68 eV) using a 400-µm elliptical spot size and a 50-eV pass-thru energy. For depth-profiling, samples of PNIPAM-b-PAA-co-PEGDA (ca. 20 mg) were pressed to 8,000 psi using a Carver Laboratory Press in a cylindrical die (0.38 cm$^2$) and transferred to the XPS platen and secured using cleaned and sonicated Cu clips. After an initial (t=0) survey and baseline scans, depth profiling commenced at 1000 eV at the instruments medium current setting, which corresponds to ca. 1 nm s$^{-1}$ for a Ta$_2$O$_5$ standard. The spectra were obtained by averaging 15 scans over the C1s, O1s, N1s, Ca2p, Na1s, and S2p regions and analyzed with AVANTAGE® software version 5.35.

Powder X-ray diffraction (XRD) was performed on powdered, dry polymeric materials using a Rigaku Smartlab Diffractometer equipped with a Cu K$\alpha$ X-ray source and a D/teX detector scanning from 15° to 80° 2 θ.

PolyHIPE Porosity—PolyHIPE materials were imaged using a scanning electron microscope to determine the scale of the pores formed during polymerization. As is common with polyHIPEs, there are two visually apparent features in these materials (FIG. 11): (i) ca. 10$^2$ µm scale spherical and hemispherical voids from the dispersed phase droplets, and (ii) ca. 10$^1$ µm scale pores from the interconnection of dispersed droplets. The micrographs reveal a clear increase in the average pore diameter with increasing molar equivalents of Ca$^{2+}$ diacrylate (relative to Na$^+$ acrylate) for the 10 wt % PNIPAM samples. Measurements of the average pore diameter were performed and the values corrected using a statistical parameter reflecting the hemispherical nature of the voids (Carnachan et al., *Soft Matter*, 2006, 2, 608-616; Shirshova et al., *J. Mater. Chem. A*, 2013, 1, 9612-9619.

Average void diameters were measured as 39.3 (±19.6), 70.4 (±20.0), 56.6 (±19.1), and 46.6 (±15.3) µm for samples with 0, 0.1, 0.2, and 0.3 equivalents of Ca$^{2+}$ diacrylate, respectively (Table 6). The porosity trend is ascribed to changes in interfacial stability of the HIPE mixtures; increasing calcium diacrylate content corresponds to a more stable interface between the aqueous continuous phase and the toluene internal phase. This observation may be due to segregation of less polar substituents to the interfacial layers (e.g. PNIPAM, PEGDA, and PEG-PPO-PEG surfactant), resulting in a more robust interface and preventing Ostwald ripening and coalescence of dispersed droplets. PNIPAM is soluble in water and toluene at room temperature, and has previously been shown to be an effective surfactant in polyHIPE materials (Oh et al., *Biomacromolecules*, 2014, 15, 1777-1787).

TABLE 6

Void and pore size analysis for 10 wt % PNIPAM series gels

| Ca$^{2+}$ diacrylate (equiv)[a] | D (µm) [b] | d (µm) [b] | d/D[c] |
|---|---|---|---|
| 0.0 | 39.3 ± 19.6 | 2.49 ± 1.06 | 0.063 |
| 0.1 | 70.4 ± 20.0 | 2.62 ± 0.38 | 0.037 |

TABLE 6-continued

Void and pore size analysis for 10 wt % PNIPAM series gels

| $Ca^{2+}$ diacrylate (equiv)[a] | D (μm) [b] | d (μm) [b] | d/D[c] |
|---|---|---|---|
| 0.2 | 56.6 ± 19.1 | 4.33 ± 1.33 | 0.076 |
| 0.3 | 46.6 ± 15.3 | 7.94 ± 1.81 | 0.170 |

[a] Equivalents relative to sodium acrylate
[b] Average diameter as determined by SEM (Cameron et al., High internal phase emulsions—Structure, properties and use in polymer preparation; In Biopolymers Liquid Crystalline Polymers Phase Emulsion, Advances in Polymer Science series 126; Springer-Verlag: Berlin, 1996, pp 163-214)
[c] Ratio of pore diameter to void diameter Average (corrected) pore diameters were 2.49 (±1.06), 2.62 (±0.38), 4.33 (±1.33), and 7.94 (±1.81) μm, for samples with 0, 0.1, 0.2, and 0.3 equivalents of calcium diacrylate, respectively, in polyHIPEs with 20 wt % PNIPAM (Table 6). The pore size increases with $Ca^{2+}$ diacrylate content, likely a result of increased gel shrinkage upon polymerization due to formation of ionic cros slinks. It is understood that a smaller droplet diameter will result in thinner continuous phase layers and increased porosity, but no significant trend is observed in pore wall measurements for these polyHIPE materials (0.903±0.28, 0.892±0.27, and 0.787±0.22 μm for 0.1, 0.2, and 0.3 equivalents of $Ca^{2+}$ diacrylate, respectively). Therefore, it seems likely that there are two complementary mechanisms that exist which explain the void and pore size observations: one of increased interfacial stability due to segregation of less polar components to the interface, and one of increased gel shrinkage upon polymerization of $Ca^{2+}$ diacrylate. The same trends are not apparent in the PNIPAM-free samples, regardless of $Ca^{2+}$ content, indicating that PNIPAM plays an important role in the interfacial stability and concomitant porosity of the polyHIPE.

PolyHIPE Component Distribution—With tenability of the porosity demonstrated, the composition of the interface between the internal and external phases was investigated by analyzing the atomic composition using XPS depth profiling. To test the hypothesis that less polar substituents preferentially segregate in proximity to the HIPE interface as a result of high $Ca^{2+}$ diacrylate loadings, a series of materials with varying ratios of PNIPAM was synthesized and XPS depth profiles were obtained for several representative polyHIPE materials (10 mol % PEGDA, 0.3 equiv $Ca^{2+}$ diacrylate, and 0-30 wt % PNIPAM, relative to Na acrylate). Atomic percentages were recorded versus etching time, with 1 s equal to 1 nm in $Ta_2O_5$. Bulk polymeric product was pressed into a pellet to yield a smooth, polyHIPE pore wall surface (collapsed upon pressing) on which XPS surface analyses were performed. Controlled etching allowed depth profiling of the polyHIPE pore walls and tracking of characteristic components of the polyHIPEs: N 1s from PNIPAM, S 2p from the trithiocarbonate chain transfer agent, and Na 1s and Ca 2p from the polyacrylate salts. Carbon is peaks were deconvoluted to determine relative amounts of ether linkages, polyacrylate/polyacrylamide backbones, carboxylates, etc. Trends in the relative atomic percentages give a qualitative view into the structure of the interface between internal and external phases in the o/w HIPE.

Figure 15:
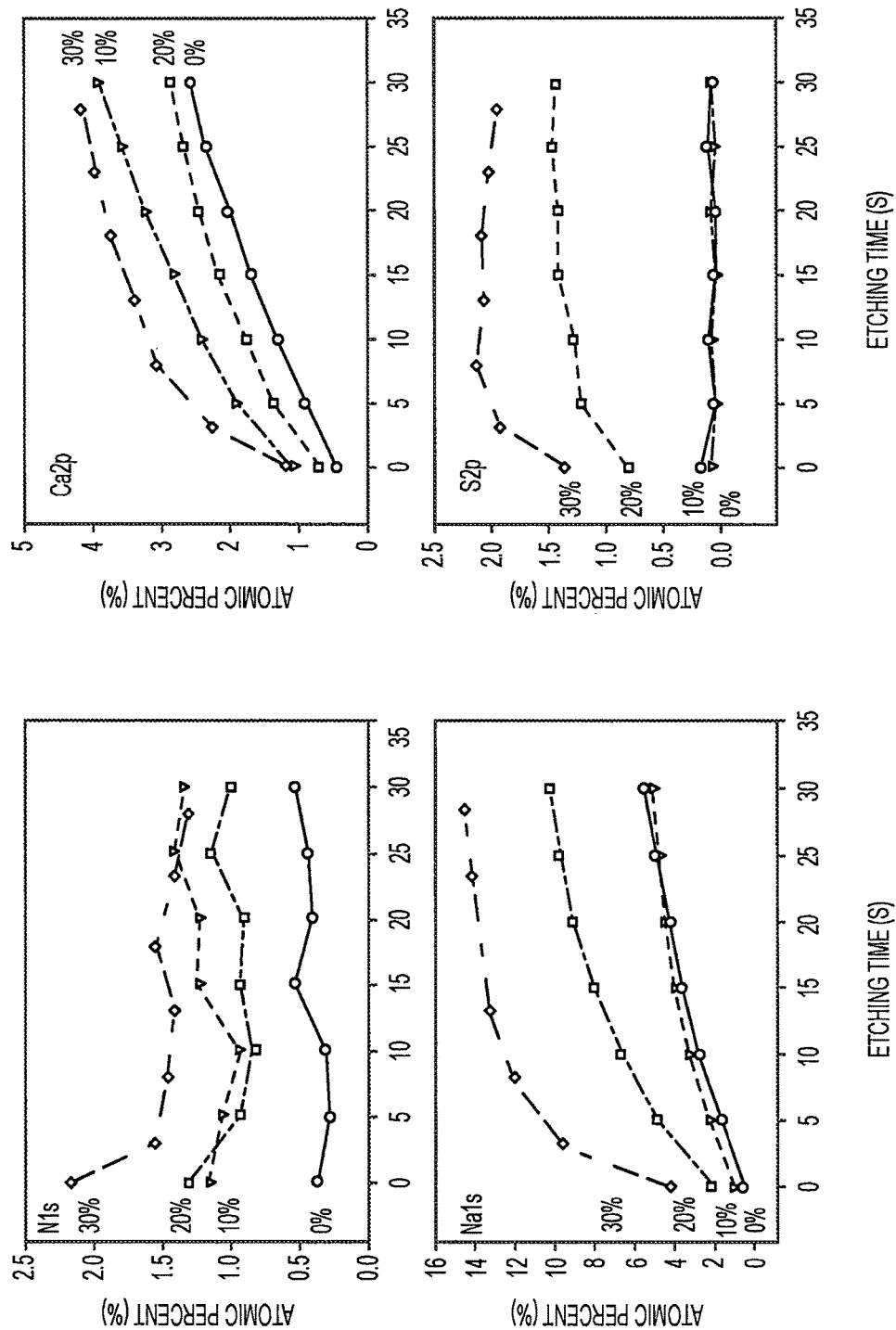
FIG. 15 shows XPS depth profiles for various polyHIPEs containing 0.3 eq. $Ca^{2+}$ diacrylate and various amounts of PNIPAM.

The relative atomic percentages of sodium and calcium (present as polyacrylates) (FIG. 15) show an increase in atomic percent (at %) at increasing depth of the pore walls. PNIPAM (as N 1s), especially evident in the 30 wt % PNIPAM polyHIPE, shows the predicted trend with a large amount present at the surface, 2.1%, and tapering to a steady level ca. (1.5%) within the continuous layer. The above observation suggests that the addition of $Ca^{2+}$ diacrylate results in segregation of less polar compounds to the interface, and confirms that PNIPAM does indeed have some surfactant-like qualities in HIPE-templated polymer synthesis. It is of importance to note that the RAFT agent is found deep within the sample and shows the inverse trend of PNIPAM, an indicator of a successful controlled radical polymerization, as opposed to a mostly free radical mechanism occurring in the interior of the aqueous phase.

Figure 16:
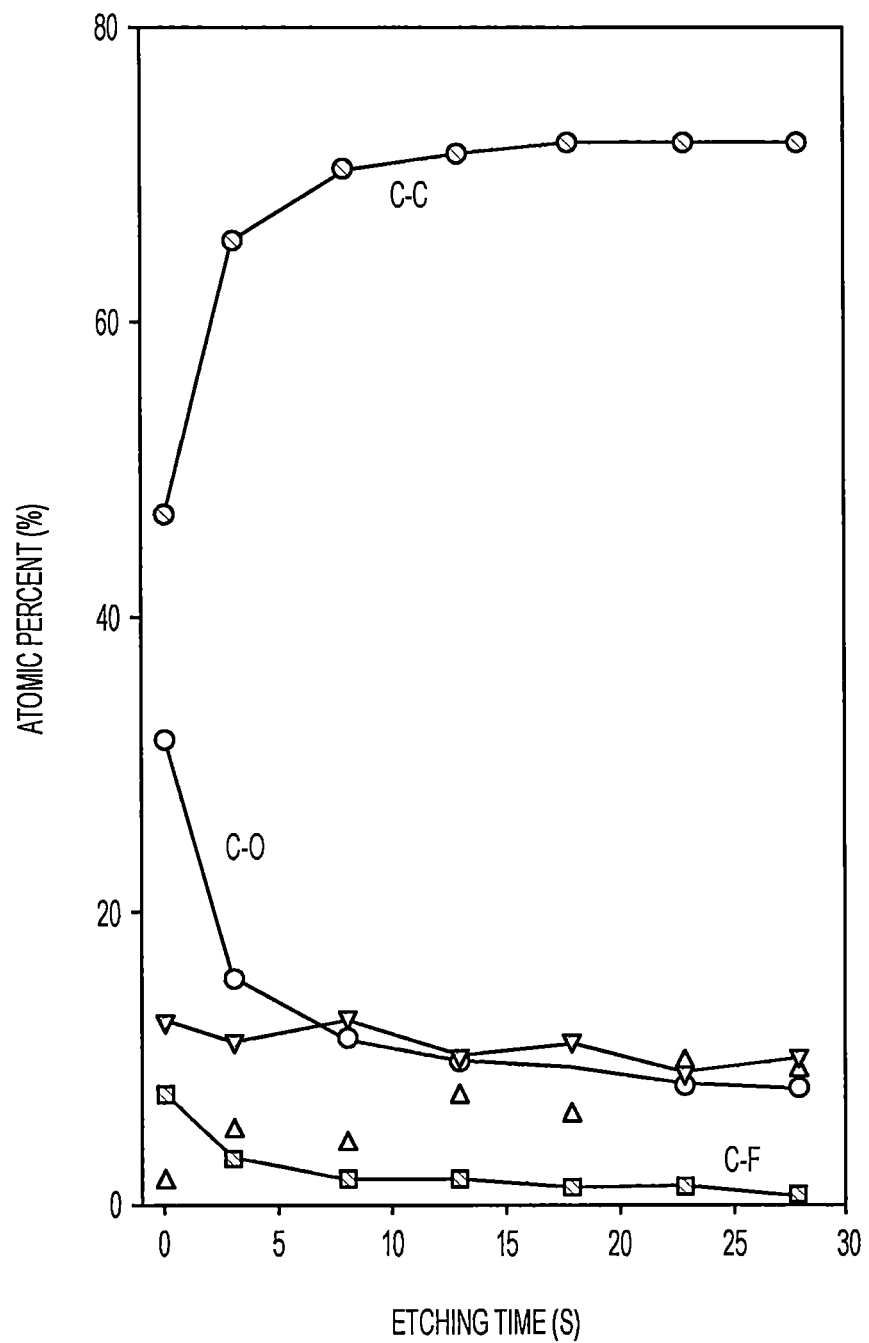
FIG. 16 shows the carbon is signal of the XPS depth profiling experiment was deconvoluted to reveal the distribution of various functional groups within the polyHIPE void walls. Sample contained 30 wt % PNIPAM and 0.3 equiv. $Ca^{2+}$ diacrylate.

Deconvolution of the C is peaks allows assignment of various functional groups to different regions of the polyHIPE void walls. As seen in FIG. 16, C—C carbons (attributed to polymer backbones of PNIPAM and polyacrylate) increase as etching depth increases, which follows the trend seen in the Na 1s and Ca 2 p signals. Since polyacrylate is the major component of the polyHIPE, this trend is expected. The ether carbon signal (C—O) is attributed to PEGDA and the PEG-PPO-PEG surfactant, and decreases with increasing depth into the void wall. Due to the mutual solubility of PEG in both the continuous and internal phase, it is reasonable that these polymers are located in the interfacial region. The distribution of the various elements suggests two non-discrete regions of crosslinking: an ionic core and an outer covalent interfacial region.

Figure 17:
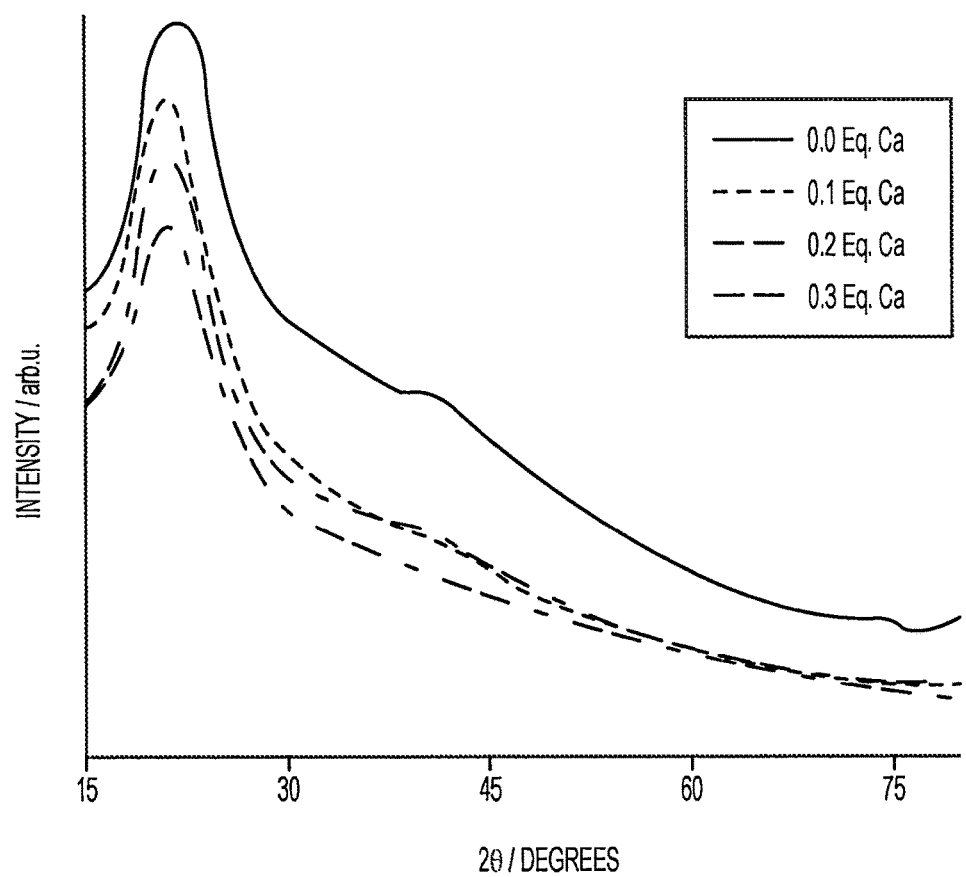
FIG. 17 shows powder X-ray diffractograms of 10 wt % PNIPAM polyHIPEs showing decrease in intensity of PEG diffraction peak with increasing $Ca^{2+}$ diacrylate content.

X-ray diffraction (XRD) of polyHIPE powders (containing 10 wt % PNIPAM) further illustrates the effect of ionic crosslinking of polyacrylate chains (FIG. 17). XRD was previously used to determine stresses in polymeric systems, with increased stress correlating to peak shifts and intensity diminution (Barret et al., Polym. Eng. & Sci., 1976, 16, 602-608; Barrett, Adv. X-Ray Anal., 1977, 20, 329-336). This trend is also seen in polyHIPE materials with increasing degrees of ionic crosslinking. The main feature is a broad diffraction peak at 2 θ=20°, with a less intense peak around 2 θ=40°, both attributed to PEG (Wang et al., Phys. Chem. Chem. Phys., 2012, 14, 13233-13238). Both diffraction peaks decrease with increasing $Ca^{2+}$ diacrylate content, which is due to either calcium complexation by PEG subunits (Pannuzzo et al., J. Chem. Phys., 2014, 140, 124905; Madsen et al., Biomaterials, 1999, 20, 1701-1708) and/or calcium-induced crosslinking during polymerization, resulting in increased gel shrinkage and disruption of PEG crystallinity. Based on the XPS depth profiling results, PEG complexation of calcium likely contributes less to the decrease in diffraction peak intensity, as PEG is found mostly at the interface, away from the calcium ions. While gel shrinkage induces stress on the interfacial components which contributes to the increased pore size and could disrupt crystallinity in the PEG-rich regions (Jeong et al., Adv. Mater., 2003, 15, 1247-1250).

Material Characterization—The mechanical properties of dry polyHIPEs were measured using a TA Instruments Q800 dynamic mechanical analyzer equipped with the film tension clamp geometry. Rectangular cuboid samples of polyHIPE were prepared using a razor blade and the dimensions measured using digital calipers; the rectangular strips (thickness approximately 3.0 mm) were carefully clamped into the DMA geometry and a frequency sweep from 0.1 to 10 Hz at 1% strain was conducted on the sample. The average storage modulus at 1 Hz (n=3) was reported for each polyHIPE composition.

Figure 18:
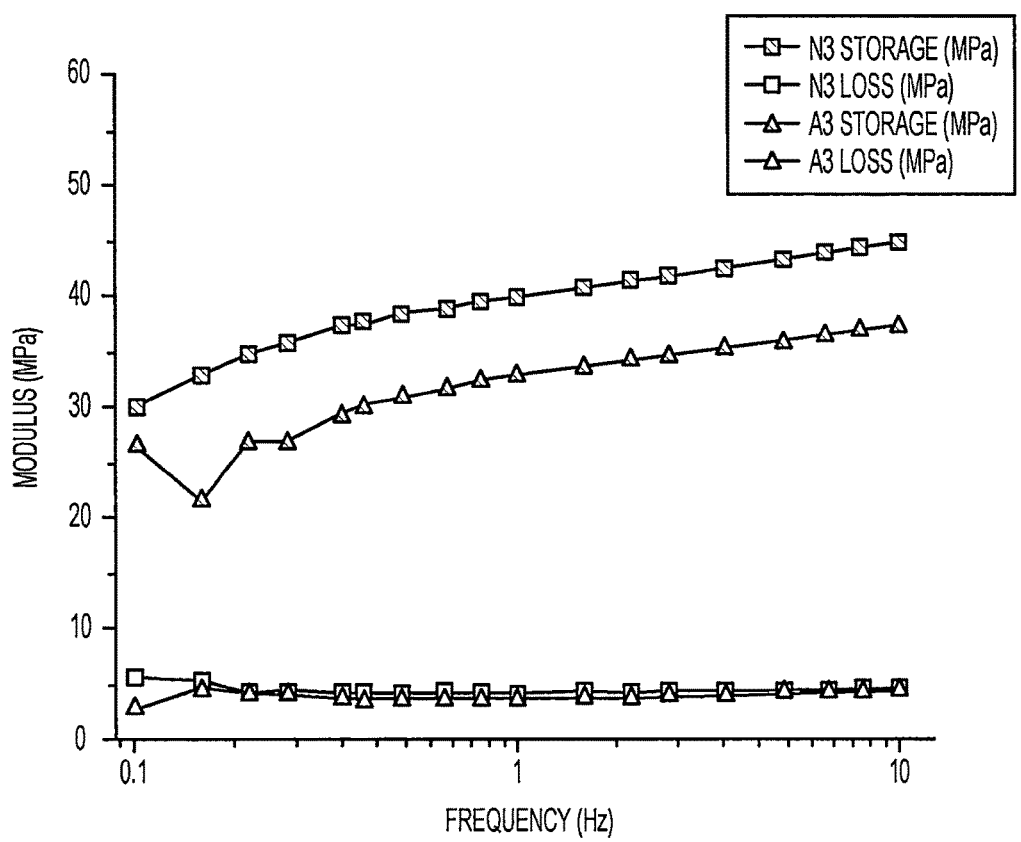
FIG. 18 shows representative tensile frequency sweeps (0.1 to 10 Hz) conducted on N3 and A3 polyHIPE compositions by dynamic mechanical analyzer.

FIG. 18 depicts a representative frequency sweep for the A3 and N3 polyHIPEs; both compositions exhibit increasing storage modulus with increasing strain rate. However, this is expected of cross-linked polymer networks, which tend to behave more elastically as chains are given less time to respond to a load force. Table 7 reports the average storage modulus acquired at the 1 Hz testing frequency and provides a general impression of the effect that composition has on polyHIPE mechanical stiffness. The A2, A3, and A5 compositions lacking PNIPAM have average storage moduli of 11.8±1.1, 27.2±5.9, and 13.4±1.5 MPa, respectively, while the N2, N3 and N5 polyHIPEs have average storage moduli of 9.8±1.1, 40.0±1.7, and 28.3±3.9 MPa, respectively. Interestingly, the N3 and N5 compositions exhibited much greater stiffness as compared to their A series counterparts. The difference may be explained by the presence of the RAFT agent that accompanies the PNIPAM prepolymer. During polyHIPE synthesis of the N series, the dormant RAFT agent may reinitiate controlled radical polymerization to form comparably longer network chains and a greater overall cross-link density; the result would be polyHIPEs with greater stiffness/elasticity. Again, the concentration of PEGDA appeared to have a counterintuitive impact on the mechanical properties: increased cross-linker content, in the A5 and N5 compositions, did not lead to greater material stiffness. Instead, the A3 and the N3 compositions had the high storage moduli in their respective series. Since these polyHIPEs are largely composed of polyacrylate chains, the addition of a non-ionic, flexible cross-linker may have a plasticizing effect at higher concentrations, a characteristic which also reflected by the decreased porosity described above.

TABLE 7

PolyHIPE Porosity, Swelling and Mechanical Properties

| HIPE Code | Porosity Void size (μm) | Porosity Pore size (μm) | Buffer Uptake (g/g) | Storage Modulus @ 1 Hz (MPa) |
|---|---|---|---|---|
| A2 | n/a | n/a | 65.5 ± 11.4 | 11.8 ± 1.1 |
| A3 | 29.6 ± 12.9 | 3.1 ± 1.6 | 24.8 ± 3.1 | 27.2 ± 5.9 |
| A5 | 28.0 ± 16.3 | 3.6 ± 1.5 | 15.7 ± 6.8 | 13.4 ± 1.5 |
| N2 | 43.5 ± 22.7 | 7.2 ± 4.9 | 38.9 ± 0.2 | 9.8 ± 1.1 |
| N3 | 36.3 ± 20.0 | 4.2 ± 2.7 | 27.6 ± 1.2 | 40.0 ± 1.7 |
| N5 | 31.7 ± 23.1 | 3.2 ± 2.1 | 18.9 ± 2.4 | 28.3 ± 3.9 |

PolyHIPE swelling analysis was performed by placing a pre-weighed rectangular piece of material (ca. 20 mg) in PBS buffer (pH 7.4) at ambient temperature overnight, then removing the swollen gel and carefully removing surface liquid with a Kim wipe before weighing. The swelling ratio was calculated using the following equation: $Q=(m_w-m_d)/m_d$, where $m_w$ is the mass of the swollen material, and is the mass of the dry material and Q is the swelling ratio. Measurements were performed in triplicate and the average ratios reported.

The absorption properties of the polyHIPEs were measured through simple equilibrium swelling studies: the foams were weighed before and after overnight immersion in PBS buffer. Table 7 summarizes the buffer uptake as a ratio of wet to dry mass of the foams. The A2, A3, and A5 foams had buffer uptake ratios of 65.5±11.4, 24.8±3.1 and 15.7±6.8, respectively, while the N2, N3 and N5 compositions had ratios of 38.9±0.2, 27.6±1.2, and 18.9±2.4, respectively. In general, the polyHIPEs exhibited buffer uptake consistent to other polyelectrolyte wound dressing materials, particularly alginates (Qin, *Journal of Applied Polymer Science* 91(2) (2004) 953-957; Jones et al., *BMJ: British Medical Journal* 332(7544) (2006) 777-780). The A2 composition swelled 65× its dry weight, but the swollen foam lacked mechanical toughness and readily disintegrated in buffer.

Cytocompatibility—The cytocompatibility of polyHIPEs was tested using a slightly modified version of ISO 10993-5 (Lundin et al., *Macromolecular Materials and Engineering* (2016) 1600375-n/a; I.T. 194, "Biological Evaluation of Medical Devices—Part 5: Tests for in Vitro Cytotoxicity (ISO 10993-5:2009)" (2009)). PolyHIPE samples, weighing approximately 5 mg, were incubated in 1.5 mL of "extract" media (EMEM supplemented with antibiotics and 10% fetal bovine serum) for a 24 hour period at 37° C., 5% $CO_2$. HeLa cells were cultured, using the same media and conditions, to 80% confluency prior to being trypsinized, lifted, and counted via hemocytometer. The cells were seeded into a 96-well TCPS plate at a density of 15,000 cells per well. The cells were incubated for five hours in 200 μL of EMEM before the media was replaced with 200 μL of the extract (or leachate); the cells were then incubated in the extract for approximately 24 hours at 37° C., 5% $CO_2$. PRESTO-BLUE™ reagent was added (20 μL) to each sample well, incubated for 45 minutes at 37° C. and the resulting fluorescence measured at 590 nm. Percent viability was normalized to a negative control of unexposed cells incubated in normal media for 24 hours. A positive control with cells incubated for two hours in EMEM media containing 1% Tween-20 solution was also included. The average percent viability reflects six independent replicate samples for each polyHIPE composition and the controls.

As a further test of cytotoxicity, a cell viability assay was performed on HeLa cells seeded to the surface of the A3 and N3 polyHIPE compositions. Circular discs of polyHIPE samples were punched from thin square sheets previously swollen in PBS buffer for 48 hours. These discs were placed on glass cover slips and enclosed by modified 0.5 mL microcentrifuge tubes (the bottom and cap were removed with scissors) to form temporary wells which were sealed with vacuum grease; this assembly allowed the "well" to be easily removed without disturbing the polyHIPE prior to imaging. During the experiments the glass coverslip "wells" were kept in 6-well TCPS plates. HeLa cells, cultured and prepared as described above, were seeded at a density of 20,000 cells per gel in 200 μL of EMEM media. Following 48 hours of incubation at 37° C. and 5% $CO_2$, calcein AM and SYTOX® Orange Dead Cell Stain (ThermoFisher, Waltham, Mass.) was added to the cells to a final concentration of 1 μM for calcein AM and 2.5 μM for SYTOX® Orange. The stains were then incubated with the cells for 25 minutes at 37° C. before microscopy was performed using a Zeiss Axio Imager 2 equipped with an Excelitas XCITE® 120 LED illuminator for fluorescent imaging. Images were taken using EC Epiplan-Neofluar 5× objective and processed using Zen Core software (Zeiss, Oberkochen, Germany). At least three independent replicates were acquired for both polyHIPE compositions.

Figure 19:
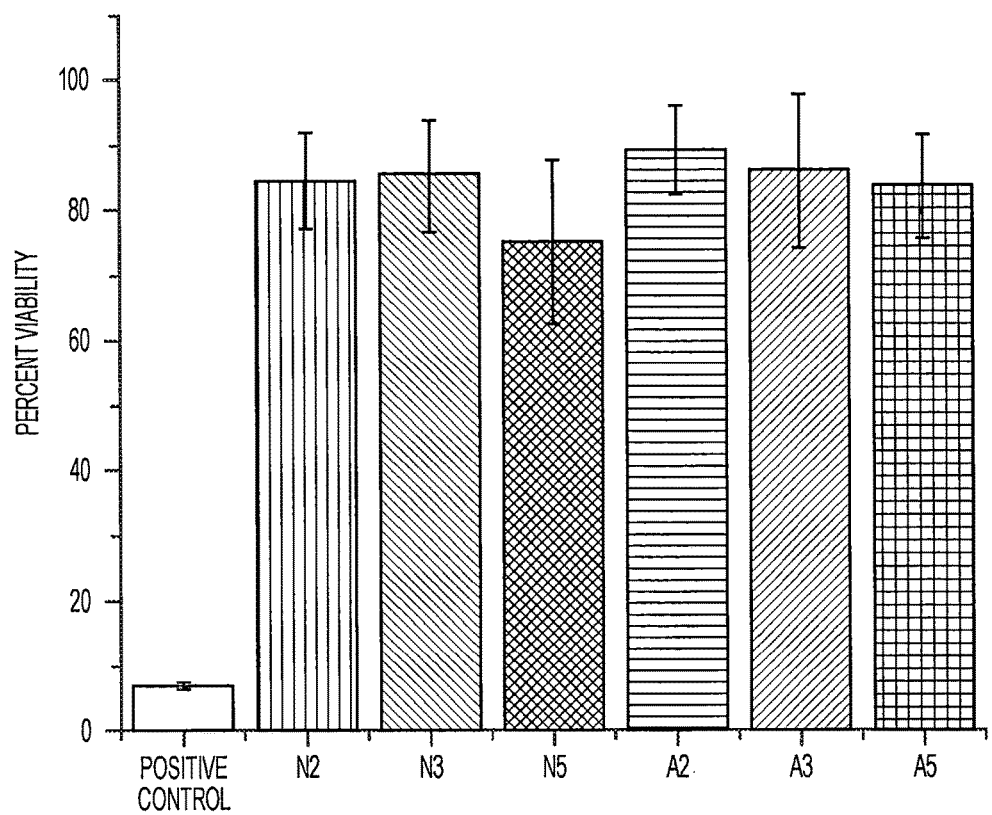
FIG. 19 shows analysis of HeLa cell viability and potential cytotoxic effects of polyHIPE foams. Results of PRESTOBLUE™ assay on the metabolic activity of cells cultured in polyHIPE media leachates for a 24 hour period illustrate minimal cytotoxicity.

Initial tests of polyHIPE cytocompatibility was performed by soaking the foams in media overnight and then incubating the media leachates with HeLa cells for a 24 hour period; decreased viability, as compared to a negative control, via a PrestoBlue assay indicated a cytotoxic effect. As depicted in FIG. 19, the polyHIPE leachates had a limited impact on the viability of the cells as for each composition the viability remained greater than 70% and are therefore considered non-toxic (Lundin et al., *Macromolecular Materials and Engineering* (2016) 1600375-n/a; I.T. 194, "Biological Evaluation of Medical Devices—Part 5: Tests for in Vitro Cytotoxicity (ISO 10993-5:2009)" (2009)). The polyHIPE materials are synthesized using potentially harmful monomers, initiators and solvents that may leach into a potential wound if not incorporated into the cross-linked material or properly removed; for example, retained toluene appeared to be a problem for cell viability early in the study. However, adjustments to the freeze-drying process and the addition of a simple ethanol wash were effective mitigating most of the toxicity.

Figure 20A:
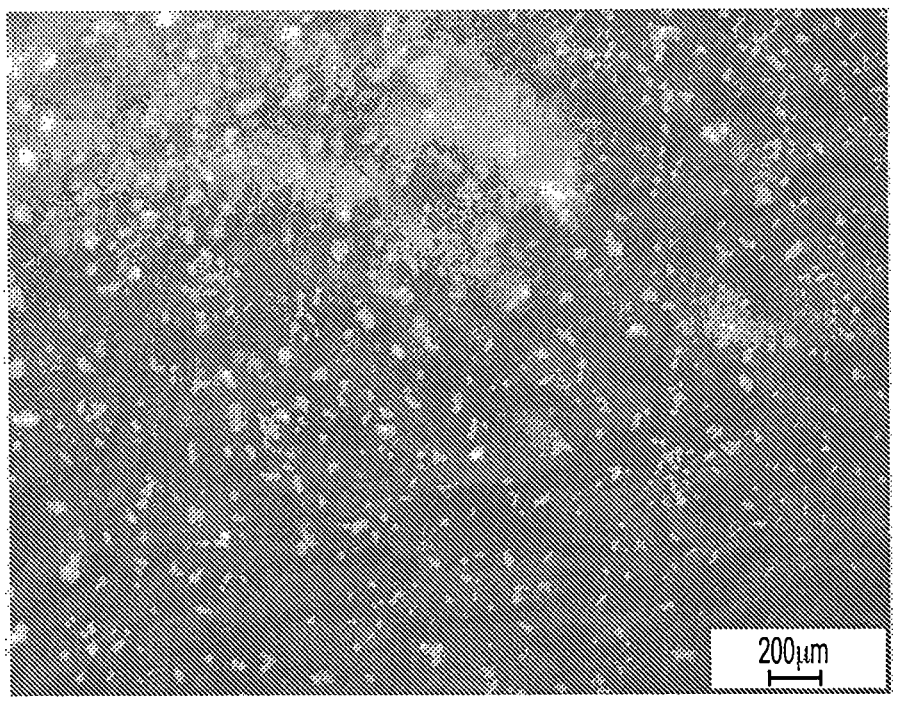
FIGS. 20A-B show representative images of cells cultured on the surface of both N3 (FIG. 20A) and A3 (FIG. 20B) swollen polyHIPE foams demonstrate the viability of cells at the end of 48 hours. The majority of cells were stained green (calcein AM), which indicates viability and only a few cells were stained red (SYTOX® Orange), indicating cell death. The objective was an EC Epiplan-Neofluar 5× objective lens and the scale bars represent 200 µm.
Figure 20B:
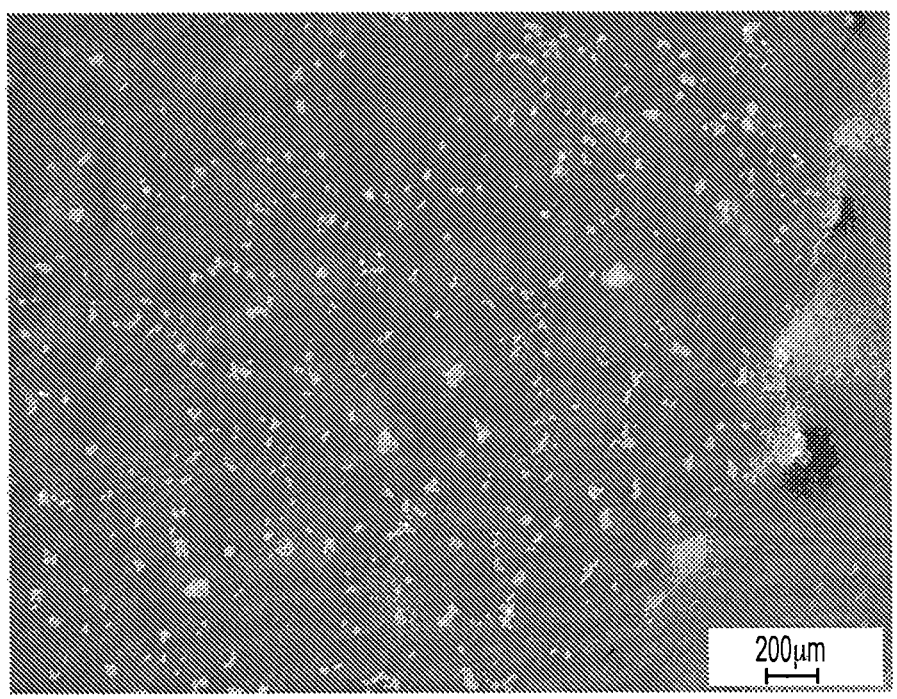

To further assess the cytocompatibility of the foams, HeLa cells were seeded to the surface of swollen N3 and A3 polyHIPEs, cultured for 48 hours and stained with cell viability dyes: calcein AM and SYTOX® Orange. FIGS. 20A-B depict representative images of the N3 and A3 cytocompatibility tests and clearly indicate that the majority of cells remain viable after two days of culture. The majority of cells did not spread on the surfaces of the polyHIPEs, but considering the lack of adhesion moieties and the composition of the foams, negatively charged polyacrylate and relatively inert PEG chains, the cells were not expected to adhere strongly. Furthermore, strong cell adhesion could complicate later wound debridement; a wound dressing may need to be cytocompatible, but ultimately it will be removed and tissue growth into the bandage, facilitated by cell adhesion, would create problems. Overall, the N3 and A3 polyHIPEs compared well against other wound dressing materials, including those based on chitosan (Ong et al., *Biomaterials* 29(32) (2008) 4323-4332) and PEG (McMahon et al., *ACS Applied Materials & Interfaces* 8(40) (2016) 26648-26656), and especially when compared to dressings loaded with silver (Ong, McMahon). Cytocompatibility is a concern for hemostatic agents and wound dressings; in particular, the toxicity of aluminum silicates presents a challenge to their application despite their blood-clotting efficacy (Bowman et al., *Journal of Trauma and Acute Care Surgery* 71(3) (2011) 727-732; Kheirabadi et al., *The Journal of Trauma* 68(2) (2010) 269-78).

Blood-clotting Index Assay—The blood-clotting efficacy of the polyHIPEs was assessed using a protocol adapted from Ong et al., *Biomaterials* 29(32) (2008) 4323-4332 and Shih et al., *International Journal of Pharmaceutics* 327(1-2) (2006) 117-125. Square polyHIPE samples, approximately 5 mm long and 0.5 mm thick, were placed at the bottom of 15 mL polypropylene conical centrifuge tubes and prewarmed to 37° C.; similarly sized cotton gauze samples were prepared as a control. Next, citrated whole blood (Innovative Research, Novi, Mich.) was briefly mixed with a 0.2 M $CaCl_2$ solution at a 10:1 ratio of blood to solution; 0.25 mL of the recalcified blood was quickly deposited on the samples and incubated for four minutes at 37° C. After four minutes, 10 mL of DI water was carefully added to the samples to resuspend and lyse the erythrocytes not trapped in the clot. Absorbance of the resulting hemoglobin solution was measured at 542 nm using a Synergy HT microplate reader (BioTek, Winooski, Vt.). Blood-clotting index (BCI) was quantified according the following equation:

$$BCI = \frac{A_w - A_s}{A_w} \times 100\% \quad (1)$$

where $A_s$ corresponds to the sample absorbance at 542 nm and $A_w$ corresponds to the average absorbance of unclotted whole blood lysed by DI water (0.25 mL of blood, 10 mL of DI water). Average BCI and error for each polyHIPE composition and gauze control correspond to five independent replicates. ANOVA and Tukey post-hoc analysis ($\alpha=0.05$) was performed using OriginLab Pro 2016 (OriginLab Corporation, Northampton, Mass.).

Figure 21:
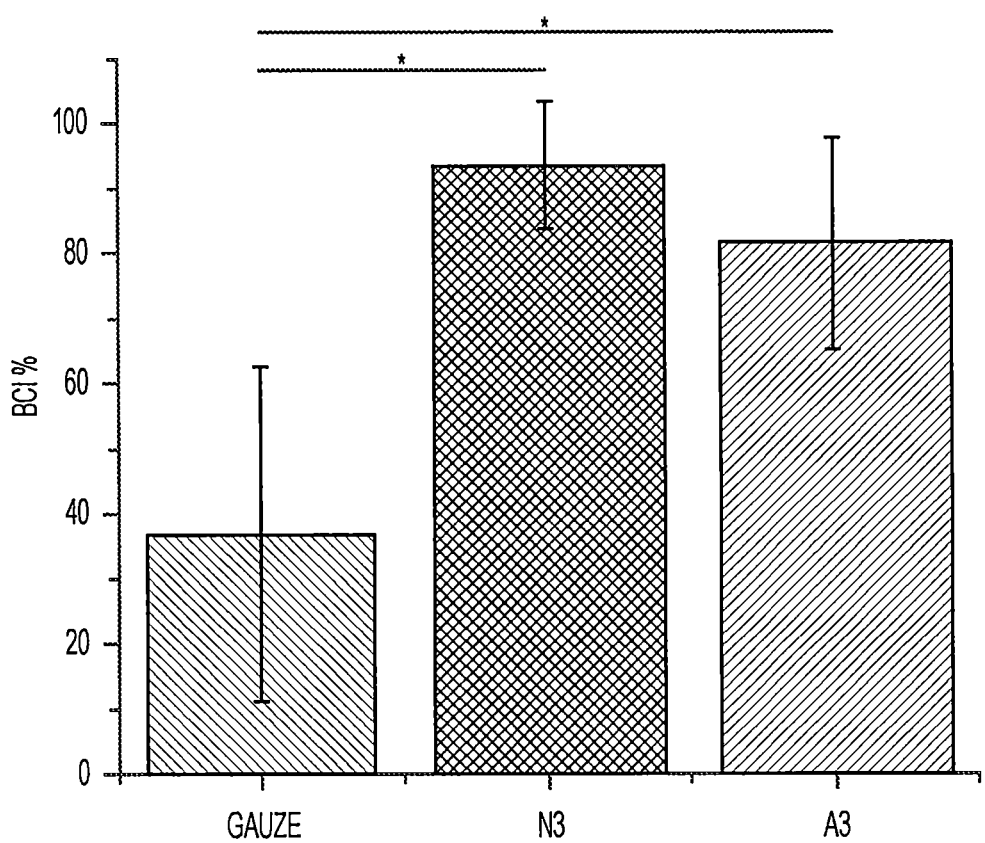
FIG. 21 shows that absorption measurements at 542 nm quantified the hemoglobin content and the average blood-clotting index (BCI) was calculated from five independent samples. The N3 and A3 polyHIPEs demonstrated significantly greater hemostatic potential than the cotton gauze (*$p<0.05$) via one-way ANOVA and Tukey post-hoc analysis.

There was a noticeable difference in the quantity of blood caught in the gauze-containing sample as compared to either of the polyHIPEs. The average blood-clotting index, reported in FIG. 21, for cotton gauze, N3, and A3 polyHIPEs were 36.7±25.7, 93.4±9.9, and 81.3±16.3 percent, respectively, and indicate the blood-clotting efficacy of N3 and A3 foams was significantly greater than for cotton gauze ($p<0.05$). The clotting ability of the polyHIPEs may be explained through the design of the material, specifically the inclusion of calcium diacrylate. As the polyHIPE foam swells in blood, calcium ions are released and, as previously mentioned, the increased the local concentration of calcium will potentiate platelet aggregation as well as other clotting factors (Hattori, et al., *Annals of Biomedical Engineering* 38(12) (2010) 3724-3732); the result appears to be a more complete clot as compared to the untreated cotton gauze. A number of biomaterials utilize calcium as a hemostatic agent, including include chitosan/alginate composites (Hattori) and modified starches (Chen et al., *Journal of Materials Chemistry B* 3(19) (2015) 4017-4026), and calcium sulfate has found application as a biocompatible hemostatic agent (Scarano et al., *Journal of endodontics* 38(1) (2012) 20-23; Scarano et al., *Journal of Oral and Maxillofacial Surgery* 68(5) (2010) 964-968).

Platelet Adhesion Assay—Adhesion of platelets to the polyHIPE surfaces was investigated using protocols adapted from previous reports (Ong et al., *Biomaterials* 29(32) (2008) 4323-4332; Shih et al., *International Journal of Pharmaceutics* 327(1-2) (2006) 117-125). Thin samples of A3 and N3 foams were cut and swollen in PBS for 24-48 hr; circular samples, approximately 5 mm in diameter, were punched from swollen films using a biopsy punch tool. Samples of cotton gauze, one ply in thickness, were cut to the same size. Platelets were either acquired directly from the vendor in the form of platelet rich plasma (PRP) or were prepared from citrated whole blood (Innovative Research, Novi, Mich.) using previously reported protocols (Ong).

A lactate dehydrogenase (LDH) assay was performed to quantify the number of platelets adhered to polyHIPE foams or cotton gauze; PRP was centrifuged for 15 minutes at 1000 g to pellet platelets that were subsequently resuspended in HEPES buffered saline (Lonza, Walkersville, Md.). Platelet concentration was measured by imaging a sample on a hemocytometer using a Zeiss Axio Imager 2 (Zeiss, Oberkochen, Germany) and counting the number of platelets with ImageJ (NIH, Bethesda, Md.). Platelets were then further diluted in HEPES buffered saline containing 2.5 mM $CaCl_2$ and 1.0 mM $MgCl_2$ before they were seeded to the polyHIPE surface at a rate of 2.5 million per sample and incubated for an hour at 37° C., 5% $CO_2$. Next, samples were removed from the platelet suspension and adhered platelets were lysed for an hour at 37° C. in 200 µL HEPES buffered saline containing 0.5% Trion X-100. Released LDH was measured according to the according to manufacturer specifications and the results were compared to a calibration curve of known quantities of lysed platelets. The reported number of adhered platelets was the average of six samples.

For the SEM analysis, platelets were prepared from citrated whole blood: briefly, blood was centrifuged at 200 g for 15 minutes at room temperature. The platelet rich portion (top) was removed and centrifuged again at 1500 g for 10 minutes. Next, platelets were resuspended in PBS and counted using the method described above. The concentration of platelets was adjusted to 12.5 million per milliliter using PBS prior to the addition of $CaCl_2$ and $MgCl_2$ at final concentrations of 2.5 mM and 1.0 mM, respectively; 100 µL (1.25 million platelets) were deposited to the surface of each sample and then incubated at 37° C. for 60 minutes. Next, the platelets were fixed in PBS containing 4% paraformaldehyde. The fixed samples were then frozen, lyophilized, and mounted on to SEM stubs using copper tape. The samples were sputter-coated with with 7 nm Au (Cressington 108 Auto, Ted Pella, Redding, Calif.) and imaged using using a JEOL-7600F field emission SEM.

Figure 22:
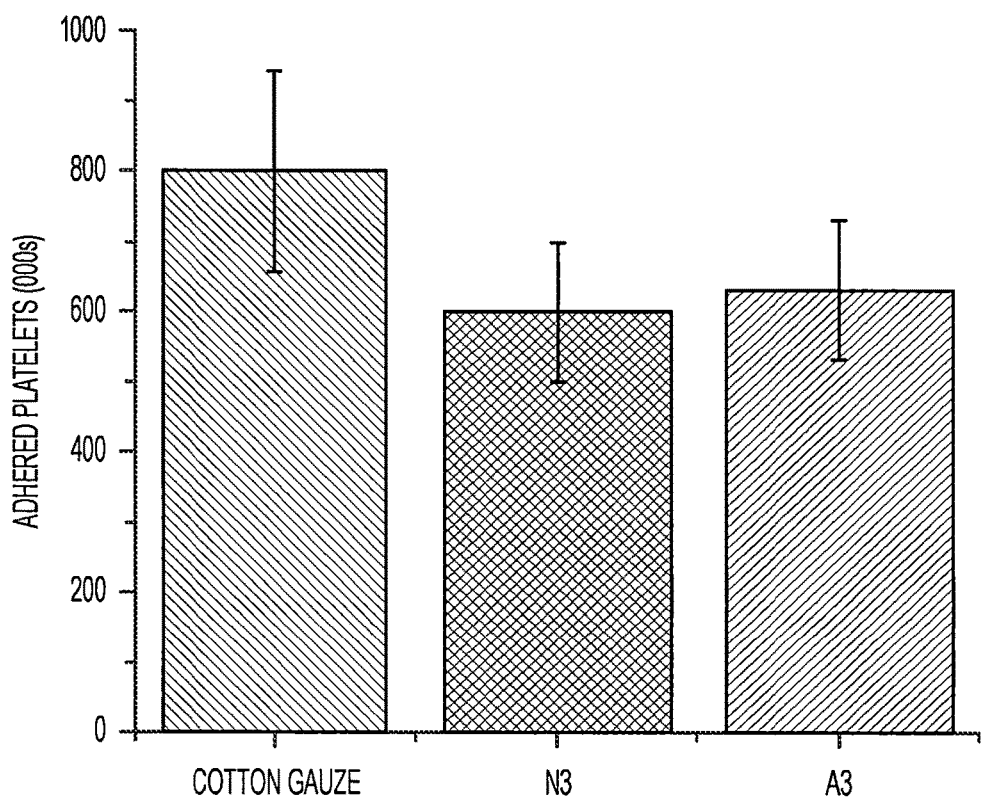
FIG. 22 average number of platelets which adhered to cotton gauze, N3 or A3 polyHIPE compositions. Each average represents six independent repeats.
Figure 23:
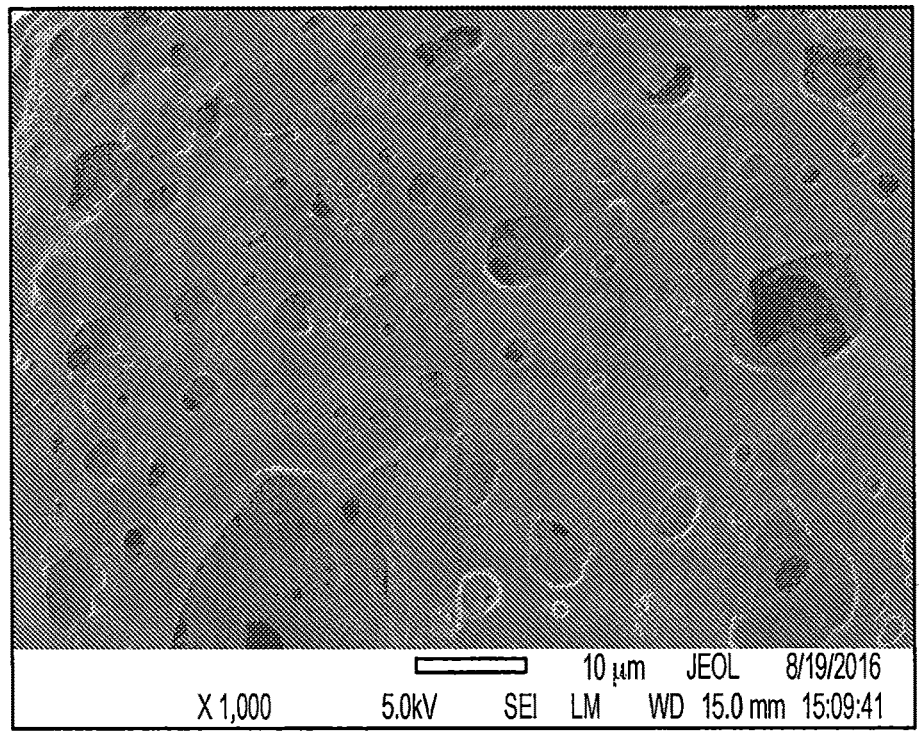
FIG. 23 shows activating platelets exhibiting a spiky morphology on the surface of A3 polyHIPEs at 1000× (top panel) and 3000× (bottom) magnification.
Figure 23:
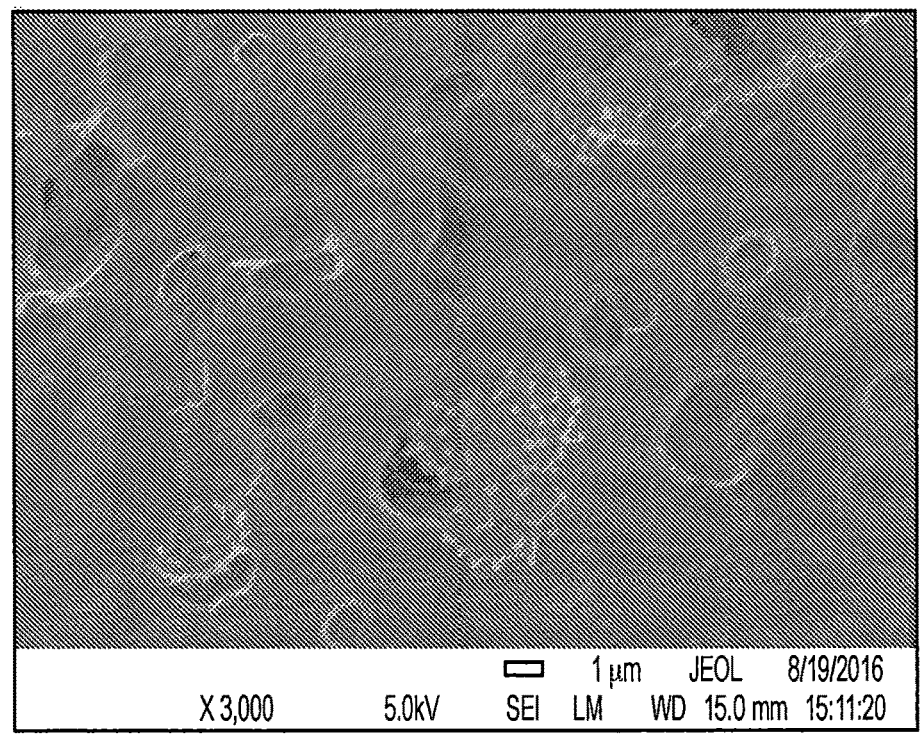

FIG. 22 depicts the average number of platelets which adhered to each dressing: 796,000±137,000 for cotton gauze, 608,000±103,000 for the N3 composition and 639,000±107,000 for the A3 composition. The polyHIPEs did not significantly differ from the cotton gauze in terms of platelet adhesion; each material tested adhered approximately 30% of the platelets in the suspension. Platelets adhered to the surface of the polyHIPEs were visualized using SEM. As depicted in FIG. 23, activating platelets, exhibiting a spiky morphology, could be visualized under high magnification on the surface of an A3 polyHIPE.

Zone-of-inhibition and Drug Delivery Assay—Antimicrobial activity of ciprofloxacin- and tetracycline-loaded polyHIPEs was assessed through a zone of inhibition assay. Dried circular discs of the A3 and N3 compositions were immersed in a 25 mL methanol solution containing either tetracycline HCl (5 mg/mL) or ciprofloxacin (1 mg/mL); to fully dissolve ciprofloxacin, 1 M HCl was added to a final concentration of 20 mM. The polyHIPE discs were incubated in the drug solutions at room temperature overnight. Prior to being frozen and lyophilized, the discs were briefly rinsed with methanol. A plate of *Staphylococcus aureus* was streaked using cells from frozen stocks; single colonies, selected from the plate, were then used to inoculate 10 mL of liquid LB media, which were cultured overnight at 37° C. The starter cultures were diluted with fresh LB to an $OD_{600}$ of approximately 1.1 before being further diluted in 1:5 ratio of culture to fresh, liquid LB media. To inoculate LB agar plates, 250 µL of the diluted culture was spread evenly across the surface of the plates, which were then incubated for 30 minutes at 37° C. The LB plates were then removed from the incubator and divided into 4 quadrants with the drug-loaded or control polyHIPE discs placed in the center of each quadrant. The plates were then returned to the incubator and cultured for approximately 24 hours. Following the 24-hour period of incubation, the plates were removed, photographed next to a standard ruler and the polyHIPEs transferred to a freshly inoculated plate which was incubated for another 24 hours. At the end of the second incubation period, the polyHIPEs were transferred once again to a new plate for a cumulative exposure period of 72 hours spread across three different plates. The diameter of the zone of inhibition was acquired from analysis of the images using ImageJ; the ruler placed next to the plate provided an internal reference for these measurements. The reported values correspond to the average of three different samples for each drug/polyHIPE composition.

Zone of inhibition investigations provided preliminary insight into the capacity of the polyHIPEs to deliver active antibiotics. In the quadrants containing the drug-loaded foams, growth of *S. aureus* cultures is inhibited in the region immediately surrounding the polyHIPE where antibiotic has diffused from the polyHIPE into the agar medium. The A3/N3 control gels do not exhibit a similar growth-inhibited region and the *S. aureus* cultures grow to the edge of polyHIPE foams in the absence of antibiotic. Interestingly, the salinity of the foams may have exerted a measure of antimicrobial activity as well. For example, there was an area of inhibited growth above the control polyHIPE where the foam was accidently dropped prior to proper centering.

Figure 24:
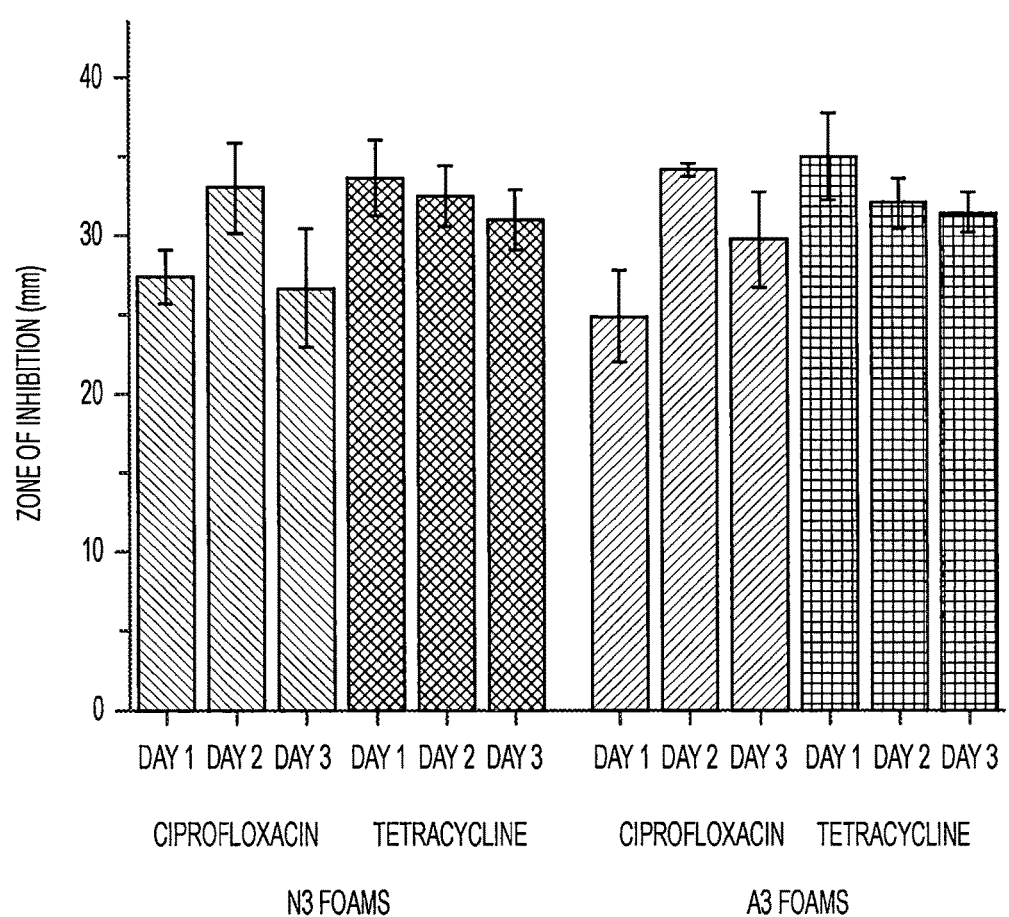
FIG. 24 shows the average diameter of the zone of inhibition for the different drug/polyHIPE compositions was consistent over a three-day period.

FIG. 24 illustrates that the zone of inhibition remained largely consistent throughout the three-day period for each of the experimental conditions. The activity of both ciprofloxacin and tetracycline within the polyHIPEs was not diminished despite incubation at 37° C. for 72 hours.

The release of antibiotics from swollen, drug loaded polyHIPE foams (N3 and A3) was assessed over a 48-hour period. Foams, previously loaded with tetracycline or ciprofloxacin using the protocol established above, were immersed into PBS buffer at a 12:1 volume to mass ratio (mL:mg) of PBS to polyHIPE foam. At each time point, 1 mL samples were removed and replaced with fresh PBS; samples were removed at 5, 10, 20, and 40 minutes as well as at 3, 6, 12, 24, 36, and 48 hours. The aliquots were analyzed via HPLC using an Agilent 1260 Infinity LC system equipped with an Agilent Poroshell 120 EC-C18 2.7 µm column (50 mm) and Agilent Infinity UV-Vis diode array detector. A gradient running from 100% water (0.1% formic acid) to 90% acetonitrile (0.1% formic acid) over 6 minutes at a rate of 0.5 mL/min was employed to elute both drugs; ciprofloxacin and tetracycline were monitored at 275 nm and 360 nm, respectively (reference wavelength was 600 nm). For both drugs, serial dilutions were analyzed to create calibration curves and all data was processed using Agilent OpenLAB CDS software prior to analysis in MS Excel and Origin 2016. Reported concentrations were corrected by adding back removed drug using the following equation:

$$C\left(\frac{\mu g}{mL}\right) = \frac{C_n V_{tot} + V_s \sum_{i}^{n-1} C_i}{V_{tot}} \quad (2)$$

where $C_n$ is the measured concentration at the current ($n^{th}$) time point, $V_{tot}$ is the total volume of the release buffer, $V_s$, is the sample volume removed at each time point and $C_i$ is the concentration of drug at $i^{th}$ time point. Each time point reports the average concentration of drug for four independent replicates.

Figure 25A:
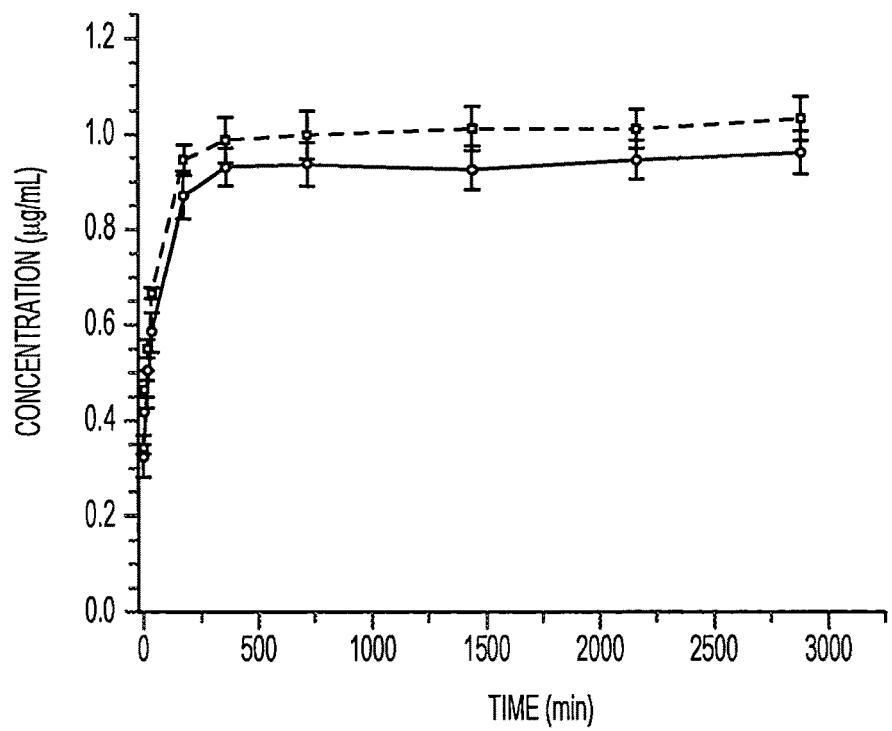
FIGS. 25A-B show drug release profiles of ciprofloxacin (FIG. 25A) and tetracycline HCl (FIG. 25B) loaded polyHIPEs. The dashed line represents the N3 composition while the solid line represents A3 composition. Each data point represents four independent replicate samples.
Figure 25B:
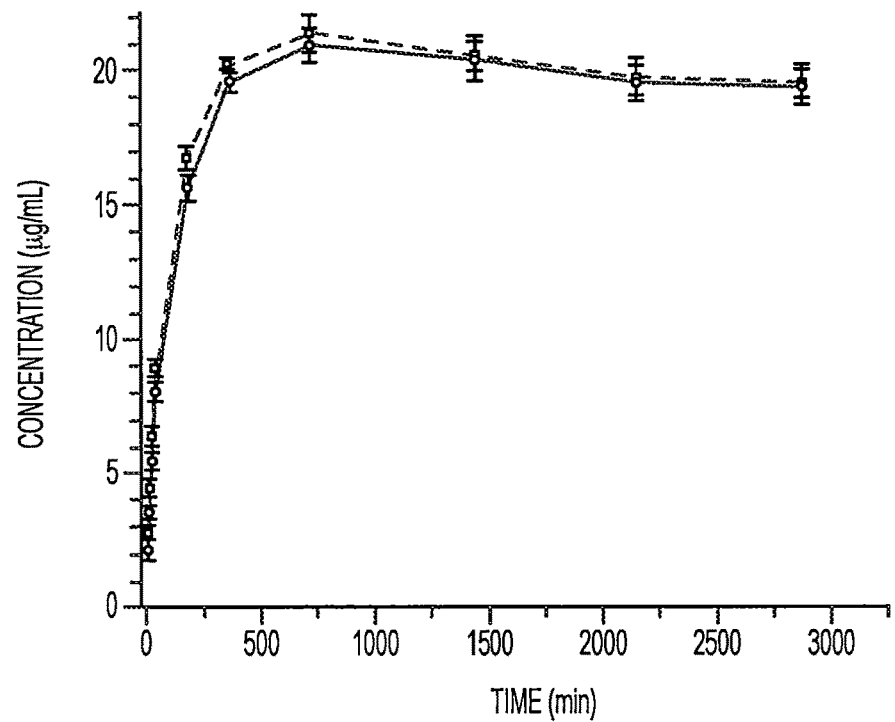

To assess the rate of antibiotic delivery for swollen polyHIPEs, drug-loaded foams were immersed in PBS buffer, which was sampled at intervals over a 48-hour period. FIGS. 25A-B depict the drug release curves for N3 and A3 polyHIPEs loaded with ciprofloxacin (FIG. 25A) and tetracycline HCl (FIG. 25B); each composition exhibited similar "burst-release" characteristics. The release curves for the ciprofloxacin-loaded polyHIPEs began to plateau after only three hours while the tetracycline-loaded foams plateaued at roughly six hours; interestingly, the presence of PNIPAM did not exert a significant influence on the kinetics of release. The polyHIPE chemistry and high degree of swelling are most probably responsible for the burst-release profile. As the polyacrylate networks expand due to the absorption of buffer, small molecule drugs are provided ample territory to diffuse from the material and without a chemistry with affinity for the drug-molecules burst-release will be the result.

For a potential wound dressing material, an initial burst-release of drug might be warranted to combat potential infections resulting from embedded debris suffered at injury. However, an ideal dressing, especially one that may need to last 72 hours with additional medical intervention, would combine initial burst-release of antibiotics with steady, sustained release. To this end, the incorporation of chitosan microparticles into the polyHIPE matrices is an ongoing effort within our laboratory (unpublished results). Previous reports illustrate how embedded-particle systems can regulate the release of drugs (Kim et al., *Biomaterials* 27(15) (2006) 3031-3037; Ki et al., *Biomedical Materials* 2(4) (2007) 269; Gu et al., *Journal of controlled release: official journal of the Controlled Release Society* 117(1) (2007) 80-9) and embedding particles within the polyHIPE foam may offer a method of incorporating sustained delivery alongside an initial burst release.

Sodium/calcium polyacrylate foams cross-linked with PEG, and including compositions with an additional PNIPAM prepolymer, were synthesized using high internal phase emulsion templating. The foam materials were found to contain the interconnected porous microstructure typical of polyHIPEs and exhibited high fluid absorption as well as mechanical stiffness in the tens of MPa range. Importantly, the polyHIPE foams were cytocompatible and exhibited impressive hemostatic activity. Platelets were found to adhere to the foams in equal number as compared to untreated cotton gauze, suggesting that clot formation is largely induced by the calcium content of the polyHIPEs. Finally, the polyHIPEs, while exhibiting burst-release under fully-swollen conditions, were capable of loading antibiotics and remained an effective antimicrobial for 72 hours at physiological relevant temperatures. Overall, the application of HIPE-templating and polyelectrolyte chemistries offers a promising alternative to the design of multifunctional wound dressing materials for serious, combat-related injuries.

Obviously, many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

What is claimed is:

1. A compound made by a method comprising:
   copolymerizing a poly(N-isopropylacrylamide) chain transfer agent, an acrylate salt, and a polyethylene glycol diacrylate.

2. The compound of claim 1, wherein the poly(N-isopropylacrylamide) chain transfer agent has a number average molecular weight of 40,000-60,000 g/mol.

3. The compound of claim 1, wherein the poly(N-isopropylacrylamide) chain transfer agent is made by a reversible addition-fragmentation chain transfer polymerization of N-isopropylacrylamide with an initiator and a chain transfer agent.

4. The compound of claim 3, wherein the initiator is 2,2'-azobisisobutyronitrile.

5. The compound of claim 3, wherein the chain transfer agent is S-dodecyl-S'-($\alpha,\alpha$'-dimethyl-$\alpha$"-acetic acid) trithiocarbonate.

6. The compound of claim 1, wherein the compound is 1-20 wt % of the poly(N-isopropylacrylamide) chain transfer agent.

7. The compound of claim 1, wherein the acrylate salt is one or more of sodium acrylate and calcium diacrylate.

8. The compound of claim 1, wherein the compound is 39-60 wt % of the acrylate salt.

9. The compound of claim 1, wherein the polyethylene glycol diacrylate has a number average molecular weight of 500-1000.

10. The compound of claim 1, wherein the compound is 28-58 wt % of the polyethylene glycol diacrylate.

11. The compound of claim 1, wherein the copolymerizing is performed by high internal phase emulsion polymerization.

12. A bandage comprising the compound of claim 1.

13. A method comprising:
    copolymerizing a poly(N-isopropylacrylamide) chain transfer agent, an acrylate salt, and a polyethylene glycol diacrylate.

14. The method of claim 13, wherein the poly(N-isopropylacrylamide) chain transfer agent is made by a reversible addition-fragmentation chain transfer polymerization of N-isopropylacrylamide with an initiator and a chain transfer agent.

15. The method of claim 13, wherein the copolymerizing is performed by high internal phase emulsion polymerization.

* * * * *